(12) United States Patent
Elangovan et al.

(10) Patent No.: US 10,335,498 B2
(45) Date of Patent: Jul. 2, 2019

(54) RNA BASED BIOMATERIAL FOR TISSUE ENGINEERING APPLICATIONS

(71) Applicant: University of Iowa Research Foundation, Iowa City, IA (US)

(72) Inventors: Satheesh Elangovan, Iowa City, IA (US); Sheetal Reginald R D'mello, Silver Spring, MD (US); Anh-Vu T Do, Iowa City, IA (US); Liu Hong, Coralville, IA (US); Behnoush Khorsand-Sourkohi, Iowa City, IA (US); Aliasger K Salem, Coralville, IA (US); Michael Kormann, Tübingen (DE)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 14/983,021

(22) Filed: Dec. 29, 2015

(65) Prior Publication Data

US 2016/0220698 A1    Aug. 4, 2016

Related U.S. Application Data

(60) Provisional application No. 62/097,405, filed on Dec. 29, 2014.

(51) Int. Cl.

| A61K 48/00 | (2006.01) |
| A61L 27/54 | (2006.01) |
| A61L 27/58 | (2006.01) |
| A61K 31/7115 | (2006.01) |
| A61K 31/712 | (2006.01) |
| A61K 38/18 | (2006.01) |
| A61K 9/50 | (2006.01) |
| A61L 27/26 | (2006.01) |
| A61K 38/00 | (2006.01) |

(52) U.S. Cl.
CPC ........ *A61K 48/0041* (2013.01); *A61K 31/712* (2013.01); *A61K 31/7115* (2013.01); *A61K 48/00* (2013.01); *A61K 48/005* (2013.01); *A61L 27/54* (2013.01); *A61L 27/58* (2013.01); *A61K 38/00* (2013.01); *A61L 2300/258* (2013.01); *A61L 2300/414* (2013.01); *A61L 2300/62* (2013.01); *A61L 2430/02* (2013.01)

(58) Field of Classification Search
None
See application file for complete search history.

(56) References Cited

U.S. PATENT DOCUMENTS

| 2011/0143397 A1* | 6/2011 | Kariko .............. A61K 48/0041 435/70.3 |
| 2012/0195936 A1 | 8/2012 | Rudolph et al. |
| 2013/0259923 A1* | 10/2013 | Bancel ................ A61K 48/005 424/450 |
| 2017/0189552 A1 | 7/2017 | Hasenpusch et al. |

FOREIGN PATENT DOCUMENTS

WO    WO-2016075154 A1    5/2016

OTHER PUBLICATIONS

Liu et al.; Design and Development of Three Dimensional Scaffolds for Tissue Engineering; Trans IChemE, Part A, Chemical Engineering Research and Design, 2007, 85(A7): 1051-1064.*
Elangovan, et al., "DNA Delivery Strategies to Promote Periodontal Regeneration", J. Biomater. Appl., 25:3, (2010).
Elangovan, Satheesh, et al., "The enhancement of bone regeneration by gene activated matrix encoding for platelet derived growth factor", Biomaterials, vol. 35, Issue 2, (2014), 737-747.
Kormann, Michael S. D., et al., "Expression of therapeutic proteins after delivery of chemically modified mRNA in mice", Nature Biotech., 29:154, (2011), 6 pgs.

* cited by examiner

*Primary Examiner* — Antonio Galisteo Gonzalez
(74) *Attorney, Agent, or Firm* — Schwegman Lundberg & Woessner, P.A.

(57) ABSTRACT

The present disclosure provides compositions and methods useful for tissue engineering including a composition having chemically modified RNA (cmRNA) encapsulated in or complexed with a non-viral delivery vehicle and a biocompatible, bioresorbable scaffold and methods of using the composition to regenerate, for example, bone tissue.

18 Claims, 4 Drawing Sheets

RNA BASED BIOMATERIAL FOR TISSUE ENGINEERING APPLICATIONS

CROSS-REFERENCE TO RELATED APPLICATIONS

This application claims the benefit of the filing date of U.S. application Ser. No. 62/097,405, filed on Dec. 29, 2014, the disclosure of which is incorporated by reference herein.

GOVERNMENT GRANT SUPPORT

This invention was made with government support under grant 1R21DE024206-01A1 awarded by the National Institutes of Health. The Government has certain rights in the invention.

BACKGROUND

The significant need for improved therapeutics promoting fracture healing and bone regeneration has led to the introduction and rapid expansion of biomimetic materials in medicine and dentistry (Deschaseaux et al., 2010; Jha et al., 2015; Wang et al., 2015; Kim et al., 2015; Vo et al., 2015; Quinlan et al., 2015; Suliman et al., 2015; Do et al., 2015). One such advancement is the introduction of growth factors or morphogens, such as bone morphogenetic protein-2 (BMP-2) (Canalis et al., 1988; Seo et al., 2015; Quinlan et al., 2015; Karfeld-Sulzer at al., 2015; Atluir et al., 2015). BMP-2 delivered as a human recombinant protein on an absorbable collagen sponge (INFUSE® Bone Graft, Medtronic Spinal and Biologics, Memphis, Tenn.) was shown to be effective in the treatment of patients with degenerative disc disease, bone fractures, as well as oral and maxillofacial osseous defects (Boyne et al., 2005: Khan et al., 2004). However, there are a number of drawbacks to using recombinant BMP-2 for both approved and off-label indications (Cancedda et al., 2007; Woo et al., 2012). In spite of its efficacy, the high cost associated with recombinant protein therapy, as well as the supraphysiological dosage required to compensate for the short half-lives of these proteins in vivo (Tannoury et al., 2014), raises serious concerns and strongly underscore the need for alternative approaches. One promising alternative is gene therapy based therapeutics. Gene therapies performed using viral vectors have demonstrated successful delivery of single or multiple transgenes for effective bone regeneration (Evans, 2010; Evans et al., 2012). Non-viral gene delivery vectors are relatively safe compared to viral vectors but have lower transfection efficiencies (Elangovan et al., 2010; Elangovan et al., 2014). The safety concerns and low transfection efficiencies associated with viral and non-viral gene therapies, respectively, are potential barriers for their clinical translation. Therefore, there is a great demand to develop regenerative strategies that are safe, cost-effective and that could potentially overcome the barriers associated with current protein and DNA based approaches.

SUMMARY

The invention provides a delivery system that may overcome many of the barriers that exist with both protein-based, as well as-DNA based, therapeutics. Employing biomaterials to release chemically modified ribonucleic acid (cmRNA) in a controlled manner addresses the high cost and safety concerns existing with recombinant protein-based approaches. By eliminating the need for nuclear trafficking (the ultimate barrier for successful DNA transfection in non-dividing cells), cmRNA delivery may address the lower transfection efficiency associated with viral or other non-viral gene delivery systems. And since in one embodiment, the strategy employs non-viral delivery vehicles, it alleviates the immunogenic concern that exists with viral vectors. Moreover, the in vivo approach rather than ex vivo transfection of cells to be modified may further reduce the overall cost.

In one embodiment, the system delivers modified RNA molecules encoding a bone or cartilage derived morphogenetic protein, for instance, bone morphogenetic protein-2 (BMP-2), to an area of therapeutic interest in the body, to promote bone or cartilage regeneration, thereby improving healing. The system includes at least modified RNA molecules, e.g., cmRNA, a non-viral delivery vehicle encapsulating or complexed with the modified RNA, which delivery vehicle optionally enhances RNA delivery to cells relative to delivery in the absence of the delivery vehicle, and a scaffold. In one embodiment, the scaffold is biocompatible. In one embodiment, the scaffold is biocompatible and bioresorbable. The scaffold allows for in vivo delivery of the modified RNA, e.g., cmRNA for BMP-2, BMP-9 or other BMPs, VEGF, PDGF or other proteins, to the target site. In one embodiment, the scaffold provides anchorage that maintains the complexed or encapsulated modified RNA molecules for a period of time in desired tissue and the modified RNA molecules complexed with or encapsulated in the delivery vehicle releases, e.g., over time, to the desired tissue. Although in one embodiment a non-viral vector may be employed to deliver RNA, viral vectors may also be employed. In one embodiment, the modified RNA is cmRNA and any cmRNA providing a therapeutic benefit may be employed, e.g., cmRNA encoding BMP-2, VEGF or PDGF. The cmRNA complexed to or encapsulated in the delivery vehicle is released from the implanted matrix and is taken up by local cells that in turn express the encoded RNA product (protein) In one embodiment, the local cells secrete the encoded protein for a therapeutic effect. All combinations of viral and non-viral delivery vehicles, and scaffolds, e.g., made from natural or synthetic polymers, may be used to deliver cmRNA.

As disclosed herein, in one embodiment, a cmRNA of BMP-2 was synthesized and complexed with a polymer nanoparticle (e.g., polyethylenimine (PEI)) to enhance uptake into cells. The transfection efficiency, cytotoxicity, osteogenic potential and in vivo bone regenerative capacity of these complexes was compared to PEI complexed with conventional plasmid DNA (encoding BMP-2). The polyplexes were fabricated at an amine (N) to phosphate (P) ratio of 10 and characterized for transfection efficiency using human bone marrow stromal cells (BMSCs). The osteogenic potential of BMSCs treated with these polyplexes was validated by determining the expression of bone-specific genes, osteocalcin and alkaline phosphatase as well as through the detection of bone matrix deposition. Using a calvarial bone defect model in rats it was shown that PEI-cmRNA (encoding BMP-2)-activated matrices promoted significantly enhanced bone regeneration compared to PEI-plasmid DNA (BMP-2)-activated matrices. The in vivo data demonstrated the potential for PEI-cmRNA complex embedded scaffolds to promote bone regeneration in vivo in adult rats thus highlighting the promising clinical potential of using cmRNA for tissue engineering applications, particularly bone regeneration. Moreover, compared to currently available biomaterials and techniques, this may be a cost-effective and safer approach to increase BMP-2 secretion for bone regeneration. For example, the system can be used in dentistry to regenerate bone prior to implant procedures. The system may also be used in orthopedics for treating fractures and bone defects from tumors or birth defects. The delivery system can be adapted easily to regenerate any other tissues of interest using cmRNA encoding a target protein of interest.

In one embodiment, the invention provides a composition comprising chemically modified RNA (cmRNA), a non-viral delivery vehicle and a scaffold. In one embodiment, the cmRNA encodes a gene product that enhances cartilage regeneration. In one embodiment, the cmRNA encodes a gene product that enhances bone regeneration. In one embodiment, the delivery vehicle comprises a synthetic polymer, e.g., comprising PEI, poly(lactic-co-glycolic acid) (PLGA) or polyamidoamine (PAMAM). In one embodiment, the delivery vehicle comprises a natural polymer, e.g., chitosan or cyclodextrin. In one embodiment, the delivery vehicle comprises a cationic polymer, for instance, PEI, chitosan, cyclodextrin or dendrimers. In one embodiment, the delivery vehicle comprises a non-cationic polymer, e.g., dioleoylphosphatidyl ethanolamine (DOPE), cholesterol, PAMAM or poloxamer. In one embodiment, the cmRNA is complexed with a cationic polymer and encapsulated into microparticles, e.g., PLGA microparticles. In one embodiment, the cmRNA is embedded in the delivery vehicle. In one embodiment, the delivery vehicle comprises microparticles. In one embodiment, the cmRNA encodes at least one of BMP-2, other BMPs, osteocalcin, type I collagen, core binding factor, VEGF, PDGF, IGF-1, IGF-2, FGF, TGF-beta, parathyroid hormone peptide, antibody to sclerostin or the antigen binding fragment thereof, antibody to receptor activator of nuclear factor kappa-B ligand (RANKL) or the antigen binding fragment thereof, or osterix. In one embodiment, the cmRNA comprises 5-methylcytidine-5'-triphosphate. In one embodiment, the cmRNA comprises pseudoundine-5'-triphosphate. In one embodiment, the scaffold comprises ceramic, a synthetic polymer or a natural polymer. In one embodiment, the scaffold is biocompatible and bioresorbable. In one embodiment, the scaffold comprises collagen.

Also provided are methods of making the compositions, e.g., by contacting, for instance, mixing, the modified RNA molecules and a delivery vehicle, to form complexes or particles, which in turn are introduced to a scaffold.

Further provided is a method to enhance tissue regeneration, e.g., cartilage or bone regeneration, in vivo or ex vivo. The method includes introducing the composition to a site in a mammal in need of repair or augmentation. In one embodiment, the tissue is a bone. In one embodiment, the composition is placed at a site of a bone defect. In one embodiment, bone density at the defect site is increased. In one embodiment, the cmRNA encodes PDGF, IGF-1, IGF-2, TGF-beta, VEGF or a BMP. In one embodiment, the defect is in a jaw bone. In one embodiment, the administration of the composition increases bone regeneration. In one embodiment, the mammal is in need of spinal fusion, fracture healing, delayed union, non-union, periodontal regeneration, ridge preservation, alveolar ridge augmentation, peri-implant bone regeneration or sinus augmentation.

DETAILED DESCRIPTION

Figure 1:
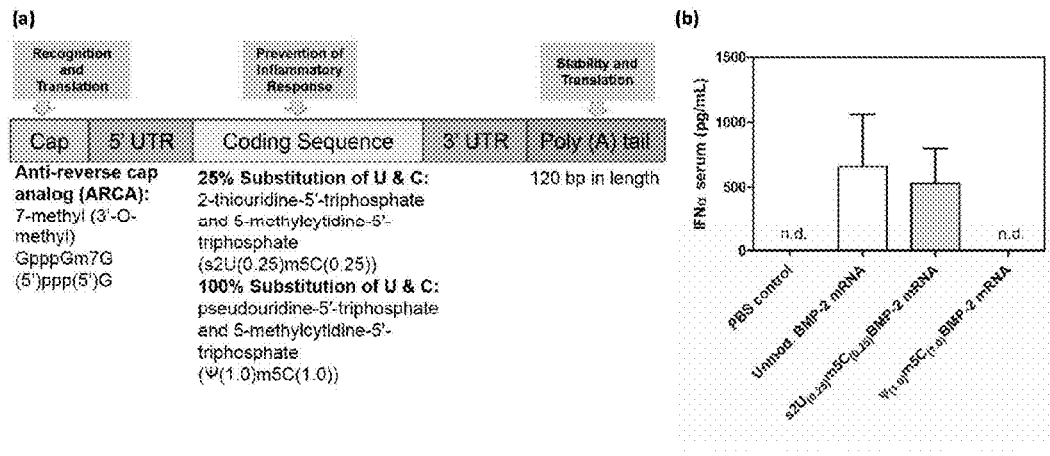
FIG. 1. (a) Scheme for modified mRNA construct with synthetic UTR and PolyA sequences attached to the coding sequence. (b) ELISA on sera to determine systemic IFN-α production 1 day following intra-peritoneal injections into BALB/c mice of 1 μg of cmRNA (s2U/m5C (25%)), Ψ/m5C (100%)), or unmodified BMP-2 mRNA (n=3). Unmodified mRNA (BMP-2) and s2U/m5C (25%) induced high levels of IFN-α which was shown to be circumvented by Ψ/m5C (100%) modifications. n.d. non-detectable. Values are expressed as mean±SD (n=3).

The dire need for improved therapeutics promoting fracture healing and bone regeneration has led to the introduction and rapid expansion of biomimetic materials in medicine and dentistry (Deschaseaux et al., 2010). One such advancement is the introduction of growth factors or morphogens, such as bone morphogenetic protein-2 (BMP-2), for clinical use (Canalis et al., 1985). BMP-2 delivered as a human recombinant protein on an absorbable collagen sponge (INFUSE® Bone Graft, Medtronic Spinal and Biologics, Memphis, Tenn.) was shown to be effective in the treatment of patients with degenerative disc disease, bone fractures, as well as oral and maxillofacial osseous defects (Boyne et al., 2005; Khan and Lande, 2004). However, there are a number of drawbacks to using recombinant BMP-2 administration for both approved and off-label indications (Woo, 2012). In spite of its efficacy, the high cost associated with recombinant protein therapy, as well as the supraphysiological dosage required to compensate for the short half-lives of these proteins in vivo (Tannoury and An, 2010), strongly underscore the need for alternative approaches. One promising alternative is a gene based therapeutic approach. Gene therapies performed using viral vectors have demonstrated successful delivery of single or multiple transgenes for effective bone regeneration (Evans, 2010). For example, gene therapy studies conducted in animals using viral vectors delivered through a traditional ex vivo or an in vivo approach have successfully demonstrated delivery of single or multiple transgenes (BMP-2 and BMP-7) are feasible and effective for bone regeneration (Evans et al., 2012; Evans, 2010). Therefore, there is an enormous demand in both medicine and dentistry to develop novel regenerative strategies that are safe, cost-effective and could potentially overcome barriers associated with current protein and DNA based approaches. Non-viral gene delivery vectors are relatively safe compared to viral vectors but have lower transfection efficiencies. The safety concerns and low transfection efficiencies associated with viral and non-viral gene therapies, respectively, are potential barriers for their clinical translation. Therefore, there is an enormous demand in both medicine and dentistry to develop regenerative strategies that are safe, cost-effective and overcome barriers associated with protein and DNA delivery.

The present disclosure provides a biomaterial that delivers modified RNA molecules such as cmRNA, e.g., cmRNA encoding BMP-2 (a potent protein involved in bone regeneration), effectively into cells for tissue engineering applications. For example, growth factors or morphogens such as BMP-2 are protein signals that help in communication between cells. Exemplary BMP genes for bone regeneration or cartilage repair, or other developmental functions, using the system of the invention are shown in Table 1.

TABLE 1

| BMP sub-family | BMP* designation | Generic name | Functions in development and musculoskeletal system |
|---|---|---|---|
| BMP2/4 | BMP2 | BMP2A | Bone & cartilage morphogenesis/heart |
|  | BMP4 | BMP2B | Bone morphogenesis |
| BMP3 | BMP3 | Ostoegenin | Negative regulator of bone density |
| BMP7 | BMP5 | BMP5 | Bone morphogenesis |

TABLE 1-continued

| BMP sub-family | BMP* designation | Generic name | Functions in development and musculoskeletal system |
|---|---|---|---|
|  | BMP6 | Vgr-1 | Bone morphogenesis, hypertrophy of cartilage/skin |
|  | BMP7 | OP-1 | Bone morphogenesis, eye and kidney development |
|  | BMP8 | OP-2 | Bone formation |
|  | BMP9 | GDF-2 | Cholinergic neuron differentiation, hepatocyte growth, hematopoiesis, bone formation |
|  | BMP10 | BMP10 | Expression restricted to heart |
|  | BMP11 | GDF-11 | A-P patterning of axial skeleton |
| GDF-5, 6, 7 | BMP12 | GDF-7 or CDMP-3 | Ligament and tendon development |
|  | BMP13 | GDF6 or CDMP-2 | Ectopic induction of tendon and ligament, cartilage development |
|  | BMP14 | GDF-5 or CDMP-1 | Join formation, chondrogenesis |
|  | BMP15 | GDF-9B | Ovulation and female fertility |

The cells that take up the cmRNA eventually produce and secrete the protein of interest. Traditionally, DNA encoding growth factors is utilized for this purpose because RNA is immunogenic when administered. The advantage of using RNA is that its activity is completely in the cytoplasm of the cells and therefore it is more predictable and efficient than DNA delivery. Moreover, RNA therapy eliminates the safety concerns that exist with gene therapy with regard to integration of DNA into the host genome. The need to have dividing mammalian cells for gene therapy to work is also eliminated with RNA delivery. In one embodiment, RNA is synthesized to avoid triggering immune responses. Such RNA, e.g., cmRNA, is used in a system that can be utilized for tissue regeneration applications.

Modified RNA Molecules for Use in the Compositions

The disclosure provides RNA molecules comprising pseudouridine or a modified nucleoside, complexes or particles comprising the modified RNA molecules and methods of using the complexes or particles or methods of using scaffolds having the complexes or particles. "Pseudouridine" includes $m^1acp^3\Psi$ (1-methyl-3-(3-amino-5-carboxypropyl)pseudouridine, (1-methylpseudouridine), $\Psi m$ (2'-O-methylpseudouridine, $m^5D$ (5-methyldihydrouridine) or $m^3\Psi$ (3-methylpseudouridine). In one embodiment, the term refers to a pseudouridine moiety that is not further modified. In another embodiment, the term refers to a monophosphate, diphosphate, or triphosphate of any of the above pseudouridines. In one embodiment, the term refers to any other pseudouridine known in the art.

In one embodiment, the present disclosure provides a messenger RNA comprising at least one pseudouridine residue. In one embodiment, the messenger RNA encodes a protein of interest. In one embodiment, the present disclosure provides in vitro transcribed RNA molecules comprising at least one pseudouridine or a modified nucleoside. In one embodiment, the present invention provides an RNA molecule encoding a protein of interest, wherein the RNA molecule comprises at least one pseudouridine residue.

In one embodiment, the present disclosure provides an in vitro synthesized RNA polynucleotide comprising a pseudouridine or a modified nucleoside, e.g., the modified nucleoside is $m^5C$, $m^5U$, $m^6A$, $s^2U$, A, or 2'-O-methyl-U. In another embodiment, the present invention provides an in vitro synthesized RNA polyribonucleotide comprising a pseudouridine and a modified nucleoside, e.g., the modified nucleoside is $m^5C$, $m^5U$, $m^6A$, $s^2U$, $\Psi$, or 2'-O-methyl-U. In another embodiment, an RNA molecule further comprises an open reading frame that encodes a functional protein. In another embodiment, the RNA molecule encodes a catalytic RNA.

In one embodiment, the RNA molecule further comprises a poly-A tail. In another embodiment, the RNA molecule does not comprise a poly-A tail.

In one embodiment, the RNA molecule further comprises a m7 GpppG cap. In another embodiment, the RNA molecule does not comprise a m77 GpppG cap.

In one embodiment, the RNA molecule further comprises a cap-independent translational enhancer. In another embodiment, the RNA molecule does not comprise a cap-independent translational enhancer. In another embodiment, the cap-independent translational enhancer is a tobacco etch virus (TEV) cap-independent translational enhancer. In one embodiment, the cap-independent translational enhancer is any other cap-independent translational enhancer known in the art.

In one embodiment, the nucleoside that is modified in a RNA molecule is uridine (U). In one embodiment, the modified nucleoside is cytidine (C). In one embodiment, the modified nucleoside is adenine (A). In another embodiment the modified nucleoside is guanine (G). In one embodiment, the modified nucleoside is $m^5C$ (5-methylcytidine). In one embodiment, the modified nucleoside is $m^5U$ (5-methyluridine). In one embodiment, the modified nucleoside is $m^6A$ ($N^6$-methyladenosine). In one embodiment, the modified nucleoside is $s^2U$ (2-thiouridine). In one embodiment, the modified nucleoside is Ψ (pseudouridine). In one embodiment, the modified nucleoside is Um (2'-O-methyluridine). In one embodiment, the RNA molecule may include combinations of modified nucleosides.

In one embodiment, the modified nucleoside is $m^5C$ (5-methylcytidine). In one embodiment, the modified nucleoside is $m^5U$ (5-methyluridine). In one embodiment, the modified nucleoside is $m^6A$ ($N^6$-methyladenosine). In one embodiment, the modified nucleoside is $s^2U$ (2-thiouridine). In one embodiment, the modified nucleoside is Ψ (pseudouridine). In one embodiment, the RNA molecule may include combinations of modified nucleosides.

In certain embodiments, up to approximately 100% of the residues in the RNA molecule are modified, for instance, up to approximately 70% of the residues modified. In another embodiment, approximately up to 65% of the residues are modified. In another embodiment, approximately up to 60% of the residues are modified. In another embodiment up to approximately 55% of the residues are modified. In another embodiment, approximately up to 50% of the residues are modified. In another embodiment, approximately up to 45% of the residues are modified. In another embodiment, approximately up to 40% of the residues are modified. In another embodiment, approximately up to 35% of the residues are modified. In another embodiment, approximately up to 30% of the residues are modified. In another embodiment, approximately up to 25% of the residues are modified. In another embodiment, approximately up to 20% of the residues are modified. In another embodiment, approximately up to 15% of the residues are modified. In another embodiment, approximately up to 10% of the residues are modified. In another embodiment, approximately up to 5% of the residues are modified. In another embodiment, approximately up to 2.5% of the residues are modified. In another embodiment, approximately up to 1% of the residues are modified.

A RNA molecule according to the invention with increased stability and diminished immunogenicity may be produced with a nucleotide mixture which contains both unmodified and also modified nucleotides, where 5 to 50% of the cytidine nucleotides and 5 to 50% of the uridine nucleotides are modified. The adenosine- and guanosine-containing nucleotides can be unmodified. A nucleotide mixture can also be used wherein some of the ATPs and/or GTPs are also modified, where their content should not exceed 20% and where their content, if present, should preferably lie in a range from 0.5 to 10%. In one embodiment, a mRNA is provided which has 5 to 50% of modified cytidine nucleotides and 5 to 50% of uridine nucleotides and 50 to 95% of unmodified cytidine nucleotides and 50 to 95% of unmodified uridine nucleotides, and the adenosine and guanosine nucleotides can be unmodified or partially modified and they are preferably present in unmodified form.

In one embodiment, 10 to 35% of the cytidine and uridine nucleotides are modified, for instance, the content of the modified cytidine nucleotides lies in a range from 7.5 to 25% and the content of the modified uridine nucleotides in a range from 7.5 to 25%. A relatively low content, e.g. only 10% each, of modified cytidine and/or uridine nucleotides may achieve the desired properties.

The nature of the modification of the nucleosides has an effect on the stability and hence the lifetime and biological activity of the mRNA. Suitable modifications are set out in Table 2:

TABLE 2

| Name | Base modification (5-position) | Sugar modification (2'-position) | Naturally in mRNA |
|---|---|---|---|
| Uridine | | | |
| 5-methyluridine 5'-triphosphate (m5U) | CH$_3$ | — | no |
| 5-idouridine 5'-triphosphate (I5U) | I | — | no |
| 5-bromouridine 5'-triphosphate (Br5U) | Br | — | no |
| 2-thiouridine 5'-triphosphate (S4U) | S (in 2 position) | — | no |
| 4-thiouridine 5'-triphosphate (S2U) | S (in 4 position) | — | no |
| 2'-methyl-2'-deoxyuridine 5'-triphosphate (U2'm) | — | CH$_3$ | yes |
| 2'-amino-2'-deoxyuridine 5'-triphosphate (U2'NH2) | — | NH$_2$ | no |
| 2'-azido-2'-deoxyuridine 5'-triphosphate (U2'N3) | — | N$_3$ | no |
| 2'-fluoro-2'-deoxyuridine 5'-triphosphate (U2'F) | — | F | no |
| Cytidine | | | |
| 5-methylcytidine 5'-triphosphate (m5C) | CH$_3$ | — | yes |
| 5-idocytidine 5'-triphosphate (I5U) | I | — | no |
| 5-bromocytidine 5'-triphosphate (Br5U) | Br | — | no |
| 2-thiocytidine 5'-triphosphate (S2C) | S (in 2 position) | — | no |
| 2'-methyl-2'-deoxycytidine 5'-triphosphate (C2'm) | — | CH$_3$ | yes |
| 2'-amino-2'-deoxycytidine 5'-triphosphate (C2'NH2) | — | NH$_2$ | no |
| 2'-azido-2'-deoxycytidine 5'-triphosphate (C2'N3) | — | N$_3$ | no |
| 2'-fluoro-2'-deoxycytidine 5'-triphosphate (C2'F) | — | F | no |
| Adenosine | | | |
| N6-methyladenosine 5'-triphosphate (m6A) | CH$_3$ (in 6 position) | — | yes |

TABLE 2-continued

| Name | Base modification (5-position) | Sugar modification (2'-position) | Naturally in mRNA |
|---|---|---|---|
| N1-methyladenosine 5'-triphosphate (m1A) | CH₃ (in 1 position) | — | no |
| 2'-O-methyladenosine 5'-triphosphate (A2'm) | — | CH₃ | yes |
| 2'-amino-2'-deoxyadenosine 5'-triphosphate (A2'NH2) | — | NH₂ | no |
| 2'-azido-2'-deoxyadenosine 5'-triphosphate (A2'N3) | — | N₃ | no |
| 2'-fluoro-2'-deoxyadenosine 5'-triphosphate (A2'F) | — | F | no |
| Guanosine | | | |
| N1-methylguanosine 5'-triphosphate (m1G) | CH₃ (in 1 position) | — | no |
| 2'-O-methylguanosine 5'-triphosphate (G2'm) | — | CH₃ | yes |
| 2'-amino-2'-deoxyguanosine 5'-triphosphate (G2'NH2) | — | NH₂ | no |
| 2'-azido-2'-deoxyguanosine 5'-triphosphate (G2'N3) | — | N₃ | no |
| 2'-fluoro-2'-deoxyguanosine 5'-triphosphate (G2'F) | — | F | no |

In one embodiment, either all uridine nucleotides and cytidine nucleotides can each be modified in the same form or else a mixture of modified nucleotides can be used for each. The modified nucleotides can have naturally or not naturally occurring modifications. A mixture of various modified nucleotides can be used. Thus, for example one part of the modified nucleotides can have natural modifications, while another part has modifications not occurring naturally or a mixture of naturally occurring modified and/or not naturally occurring modified nucleotides can be used. Also, a part of the modified nucleotides can have a base modification and another part a sugar modification. In the same way, it is possible that all modifications are base modifications or all modifications are sugar modifications or any suitable mixture thereof. By variation of the modifications, the stability and/or duration of action of the RNA according to the invention can be selectively adjusted.

In one embodiment of the invention, at least two different modifications are used for one type of nucleotide, where one type of the modified nucleotides has a functional group via which further groups can be attached. Nucleotides with different functional groups can also be used, in order to provide binding sites for the attachment of different groups. Thus for example a part of the modified nucleotides can bear an azido group, an amino group, a hydroxy group, a thiol group or some other reactive group which is suitable for reaction under predefined conditions. The functional group can also be such that it can under certain conditions activate a naturally present group capable of binding, so that molecules with functions can be coupled. Nucleotides which are modified so that they provide binding sites can also be introduced as adenosine or guanosine modifications. The selection of the particular suitable modifications and the selection of the binding sites to be made available depends on what groups are to be introduced and with what frequency these are to be present. Thus the content of the nucleotides provided with functional and/or activating groups depends on how high the content of groups to be coupled is to be and can easily be determined by those skilled in the art. As a rule, the content of nucleotides modified with functional and/or activating groups, if present, is 1 to 25% of the modified nucleotides. Those skilled in the art can if necessary determine the most suitable groups in each case and the optimal content thereof by routine experiments.

In one embodiment, a combination of 2'-thiouridine as a modified uridine-containing nucleotide and 5'-methylcytidine as a modified cytidine nucleotide is employed. In one embodiment, these two nucleotides are each present at a content of 10 to 30%. Nucleotides modified in another way can optionally also be present, as long as the total content of modified nucleotides does not exceed 50% of the particular nucleotide type. In one embodiment, a polyribonucleotide has 5 to 50%, e.g., 5 to 30% or 7.5 to 25%, of the uridine nucleotides as T-thiouridine nucleotides, and 5 to 50%, e.g., 5 to 30% or 7.5 to 25%, of the cytidine nucleotides as 5'-methylcytidine nucleotides, where the adenosine and guanosine nucleotides can be unmodified or partially modified nucleotides. In one embodiment, this mRNA according to the invention additionally has a 7'-methylguanosine cap and/or a poly(A) end. Thus, in one embodiment the mRNA is produced in its mature form, i.e with a GppG cap, an IRDS and/or a polyA tail.

In many cases, as stated above, for the improvement of immunogenicity and stability or for adjustment of properties it can be beneficial to combine modified nucleosides with functional groups, which provide binding sites, with non-functionally modified nucleosides. If functionally modified nucleosides are desired, 2'-azido and 2'-amino nucleosides may be employed.

In one embodiment, the cytidine nucleotides and/or uridine nucleotides can have a modification which creates a binding site, such as for example azido, NH, SH or OH groups.

In one embodiment, the length of a RNA molecule is greater than 30 nucleotides in length. In another embodiment, the RNA molecule is greater than 35 nucleotides in length. In another embodiment, the length is at least 40 nucleotides. In another embodiment, the length is at least 45 nucleotides. In another embodiment, the length is at least 55 nucleotides. In another embodiment, the length is at least 60 nucleotides. In another embodiment, the length is at least 60 nucleotides. In another embodiment, the length is at least 80 nucleotides. In another embodiment, the length is at least 90 nucleotides. In another embodiment, the length is at least 100 nucleotides. In another embodiment, the length is at least 120 nucleotides. In another embodiment, the length is at least 140 nucleotides. In another embodiment, the length is at least 160 nucleotides. In another embodiment, the length is at least 180 nucleotides. In another embodiment, the length is at least 200 nucleotides. In another embodiment, the length is at least 250 nucleotides. In another embodiment, the length is at least 300 nucleotides. In another embodiment, the length is at least 350 nucleotides. In another embodiment, the length is at least 400 nucleotides. In another embodiment, the length is at least 450 nucleotides. In another embodiment, the length is at least 500 nucleotides. In another embodiment, the length is at least 600 nucleotides. In another embodiment, the length is at least 700 nucleotides. In another embodiment, the length is at least 800 nucleotides. In another embodiment, the length is at least 900 nucleotides. In another embodiment, the length is at least 1000 nucleotides. In another embodiment, the length is at least 1100 nucleotides. In another embodiment, the length is at least 1200 nucleotides. In another embodiment, the length is at least 1300 nucleotides. In another embodiment, the length is at least 1400 nucleotides. In another embodiment, the length is at least 1500 nucleotides. In another embodiment, the length is at least 1600 nucleotides. In another embodiment, the length is at least 1800 nucleotides. In another embodiment, the length is at least 2000 nucleotides. In another embodiment, the length is at least 2500 nucleotides. In another embodiment, the length is at least 3000 nucleotides. In another embodiment, the length is at least 4000 nucleotides. In another embodiment, the length is at least 5000 nucleotides. In one embodiment, the length is less than 10,000 nucleotides. In one embodiment, the length is at least 100 nucleotides up to 8,000 nucleotides.

Uses for the Modified RNA Molecules

According to the disclosure, a RNA molecule with partially multiply modified nucleotides, and the use of the RNA molecules for the production of a gene product for the treatment of diseases due to deficient or defective genes or for the treatment of diseases or disorders which can be moderated or cured by the provision of RNA or proteins in vivo, such as factors, stimulators, inducers or enzymes, are provided. Thus, a RNA molecule with increased stability and/or decreased immunogenicity is provided for use in the systems of the invention. The RNA according to the invention contains a ribonucleotide sequence which, in one embodiment, encodes a protein or fragment thereof whose function in the cell or in the vicinity of the cell is needed or beneficial, e.g., a protein the lack or defective form is a trigger for a disease or an illness, that can moderate or prevent a disease or an illness, or a can promote a process which is beneficial for the body, in a cell or its vicinity. In one embodiment, the RNA according to the invention contains the sequence for the complete protein or a functional variant thereof. Further, the ribonucleotide sequence can encode a protein which acts as a factor, inducer, regulator, stimulator or enzyme, or a functional fragment thereof, where this protein is one whose function is necessary in order to remedy a disorder or in order to initiate processes in vivo such as the formation of new bone development, blood vessels, or other tissues, etc. Here, functional variant can undertake the function of the protein whose function in the cell is needed or the lack or defective form thereof is pathogenic. In addition, the RNA molecule can also have further functional regions and/or 3' or 5' noncoding regions. The 3' and/or 5' noncoding regions can be the regions naturally flanking the encoded protein or else artificial sequences which contribute to the stabilization of the RNA. Those skilled in the art can discover the sequences suitable for this in each case by routine experiments.

Thus, the RNA molecule may be used for the therapy of diseases or for the provision of proteins beneficial to the body. When the RNA molecule is used for the therapy of diseases, its expression in a cell in a tissue may leads to the moderation of an illness. For example, the RNA may encode a protein or protein fragment the presence thereof can moderate an illness or be beneficial or supportive to the body, for instance, because there is not sufficient protein or not sufficient function (nonpathogenic) protein or because the protein or fragment can benefit the body under certain conditions, e.g. in the treatment of defects or in the context of implantation. These include altered forms of proteins or protein fragments, i.e., forms of proteins which may alter in the course of the metabolism, e.g., matured forms of a protein, etc. Proteins which play a part in growth processes and angiogenesis, which are for example necessary in controlled regeneration and can then be formed specifically by introduction of the mRNA according to the invention, can also be provided. This can, for example, be useful in growth processes or for the treatment of bone defects, tissue defects and in the context of implantation and transplantation.

The mRNA modified according to the invention may be used in order to promote the ingrowth of implanted prostheses. If it is available on the surface of prostheses to be inserted such as tooth implants, hip endoprostheses, knee endoprostheses or vertebral fusion bodies, the mRNA according to the invention can release factors which can promote the ingrowth, new formation of blood vessels and other functions which are necessary for the newly inserted prostheses. Thus, for example the administration of biologically active substances such as growth factors such as BMP-2 or angiogenesis factors in the context of implantation of prostheses or thereafter is known. Since biological substances very often have extremely short half-lives, it was previously necessary to use very high dosages, which burdens the patient with severe side effects. According to the invention, this disadvantage is avoided since using the RNA according to the invention the desired and/or needed proteins can be used selectively and suitably dosed. This decreases or even completely spares the patient the side effects. In this embodiment, the RNA according to the invention which encodes desired and/or needed substances such as growth factors, angiogenesis factors etc. can be applied onto the implant in a coating releasing the RNA in a measured manner and then released gradually therefrom in a measured manner, so that the cells in the vicinity of the implant can continuously or intermittently produce and if necessary release the desired factors. Polylactide or polylactide/glycolide polymers may, for example, be used as a delivery vehicle. In this way it is possible selectively to release the desired factors continuously, intermittently, over a longer or shorter time and at the desired site.

In the context of the present invention, a deficient or defective gene or deficiency or lack are understood to mean genes which are not expressed, incorrectly expressed or not expressed in adequate quantity and as a result cause diseases or illnesses, e.g. by causing metabolic disorders.

A further field in which the RNA according to the invention can be used is the field of regenerative medicine. Through disease processes or through aging, degenerative diseases arise which can be treated and moderated or even cured by introduction of proteins produced too little or not at all owing to the disease or aging processes. By introduction of the relevant RNA encoding these proteins, the degenerative process can be halted or regeneration can even be initiated. Examples of this are growth factors for tissue regeneration which can be used e.g. in growth disorders, in degenerative diseases such as osteoporosis, arthritis or impaired wound healing. Here, the present system offers not only the advantage that the missing protein can be provided selectively and in the correct dosage but in addition it is possible to provide the protein in a certain time window. Thus, for example, with impaired wound healing, the relevant healing factor or growth factor can be provided for a limited time by dosed administration of the RNA molecule. In addition, it can be arranged that the RNA is selectively brought to the site of its desired action.

Examples of factors which can be expressed using the modified RNA molecule so as to have a regenerative action include but are not limited to fibroblast growth factor (FGF), e.g., bFGF, transforming growth factor (TGF), TGF-α and TGF-β, BMPs (bone morphogenetic protein), e.g., BMP1 to 7, 8a and b, 9, 10, and other BMPs, platelet-derived growth factor (PDGF), e.g., PDGF-A, PDGF-B, PDGF-C and PDGF-D, epidermal growth factor (EGF), granulocyte-macrophage colony stimulating factor (GM-CSF), vascular endothelial growth factor (VEGF-A to F and PIGF), insulin-like growth factors, e.g. IGF1 and IGF2, hepatocyte growth factor (HGF), interleukins, e.g. interleukin-1B, IL-8 and IL-1 to IL-31, nerve growth factor (NGF) and other factors which stimulate the formation of erythrocytes, neutrophils, blood vessels, etc.

In one embodiment, to enhance ligament repair, the modified RNA molecule may encode one or more of VEGF, PDGF, IGF-1, EGF, TGF-beta, or bFGF.

In one embodiment, to enhance tendon repair, the modified RNA molecule may encode one or more of VEGF, PDGF, IGF-1, EGF, TGF-beta, or bFGF.

In one embodiment, to enhance cardiac repair, the modified RNA molecule may encode one or more of NGF, bFGF, IGF1 or neuregulin.

In one embodiment, to enhance muscle repair, the modified RNA molecule may encode one or more of TNF-alpha, bFGF, IGF-I, NGF, PDGF, EGF, or BMP.

In one embodiment, to enhance bone repair, the modified RNA molecule may encode one or more of BMP-1 to 9, core binding factor, VEGF, PDGF, IGF-1, IGF-2, FGF, TGF-beta, antibody to sclerostin or the antigen binding fragment thereof, or antibody to receptor activator of nuclear factor kappa-B ligand (RANKL) or the antigen binding fragment thereof.

In one embodiment, to enhance liver repair, the modified RNA molecule may encode one or more of HGF, TNF-alpha, IL6, bFGF, VEGF, IGFI, IGFII, TGF-beta, BMP, or activin.

"Effective amount" of a RNA molecule refers to an amount sufficient to exert a therapeutic effect. In one embodiment, the term refers to an amount sufficient to elicit expression of a detectable amount of the recombinant protein.

Exemplary Non-Viral Delivery Vehicles

In one embodiment, a non-viral delivery vehicle comprises inorganic nanoparticles, e.g., calcium phosphate or silica particles; polymers including but not limited to poly (lactic-co-glycolic acid) (PLGA), polylactic acid (PLA), linear and/or branched PEI with differing molecular weights (e.g., 2, 22 and 25 kDa), dendrimers such as polyamidoamine (PAMAM) and polymethoacrylates; lipids including but not limited to cationic liposomes, cationic emulsions, DOTAP, DOTMA, DMRIE, DOSPA, distearoylphosphatidylcholine (DSPC), DOPE, or DC-cholesterol; peptide based vectors including but not limited to Poly-L-lysine or protamine; or poly(β-amino ester), chitosan, PEI-polyethylene glycol, PEI-mannose-dextrose, DOTAP-cholesterol or RNAiMAX.

In one embodiment, the delivery vehicle is a glycopolymer-based delivery vehicle, poly(glycoamidoamine)s (PGAAs), that have the ability to complex with various polynucleotide types and form nanoparticles. These materials are created by polymerizing the methylester or lactone derivatives of various carbohydrates (D-glucarate (D), meso-galactarate (G), D-mannarate (M), and L-tartarate (T)) with a series of oligoethyleneamine monomers (containing between 1-4 ethylenamines (Liu and Reineke, 2006). A subset composed of these carbohydrates and four ethyleneamines in the polymer repeat units yielded exceptional delivery efficiency.

In one embodiment, the delivery vehicle comprises polyethyleneimine (PEI), Polyamidoamine (PAMAM), PEI-PEG, PEI-PEG-mannose, dextran-PEI, OVA conjugate, PLGA microparticles, or PLGA microparticles coated with PAMAM.

In one embodiment, the delivery vehicle comprises a cationic lipid, e.g., N-[1-(2,3-dioleoyloxy)propel]-N,N,N-trimethylammonium (DOTMA), 2,3-dioleyloxy-N-[2-spermine carboxamide] ethyl-N,N-dimethyl-1-propanammonium trifluoracetate (DOSPA, Lipofectamine); 1,2-dioleoyl-3-trimethylammonium-propane (DOTAP); N-[1-(2,3-dimyristloxy) propyl]; N,N-dimethyl-N-(2-hydroxyethyl) ammonium bromide (DMRIE), 3-β-[N—(N,N'-dimethylaminoethane) carbamoyl] cholesterol (DC-Chol); dioctadecyl amidoglyceryl spermine (DOGS, Transfectam); or imethyldioctadeclyammonium bromide (DDAB). The positively charged hydrophilic head group of cationic lipids usually consists of monoamine such as tertiary and quaternary amines, polyamine, amidinium, or guanidinium group. A series of pyridinium lipids have been developed (Zhu et al., 2008; van der Woude et al., 1997; Ilies et al., 2004). In addition to pyridinium cationic lipids, other types of heterocyclic head group include imidazole, piperizine and amino acid. The main function of cationic head groups is to condense negatively charged nucleic acids by means of electrostatic interaction to slightly positively charged nanoparticles, leading to enhanced cellular uptake and endosomal escape.

Lipids having two linear fatty acid chains, such as DOTMA, DOTAP and SAINT-2, or DODAC, may be employed as a delivery vehicle, as well as tetraalkyl lipid chain surfactant, the dimer of N,N-dioleyl-N,N-dimethyl-ammonium chloride (DODAC). All the trans-orientated lipids regardless of their hydrophobic chain lengths ($C_{16:1}$, $C_{18:1}$ and $C_{20:1}$) appear to enhance the transfection efficiency compared with their cis-orientated counterparts.

The structures of cationic polymers useful as a delivery vehicle include but are not limited to linear polymers such as chitosan and linear poly(ethyleneimine), branched polymers such as branch poly(ethyleneimine) (PEI), circle-like polymers such as cyclodextrin, network (crosslinked) type polymers such as crosslinked poly(amino acid) (PAA), and dendrimers. Dendrimers consist of a central core molecule, from which several highly branched arms 'grow' to form a tree-like structure with a manner of symmetry or asymmetry. Examples of dendrimers include polyamidoamine (PAMAM) and polypropylenimine (PPI) dendrimers.

DOPE and cholesterol are commonly used neutral co-lipids for preparing cationic liposomes. Branched PEI-cholesterol water-soluble lipopolymer conjugates self-assemble into cationic micelles. Pluronic (poloxamer), a non-ionic polymer and SP1017, which is the combination of Pluronics L61 and F127, may also be used.

In one embodiment, PLGA particles are employed to increase the encapsulation frequency although complex formation with PLL may also increase the encapsulation efficiency. Other cationic materials, for example, PEI, DOTMA, DC-Chol, or CTAB, may be used to make nanospheres.

In one embodiment, no delivery vehicle is employed, e.g., naked cmRNA is employed alone or with a scaffold.

In one embodiment, physical methods including but not limited to electroporation, sonoporation, magnetoporation, ultrasound or needle injection may be employed to introduce naked cmRNA, complexes of cmRNA and a delivery vehicle or cmRNA encapsulated in particles, or a scaffold having complexes of cmRNA and a delivery vehicle or cmRNA encapsulated in particles, into a tissue.

Exemplary Scaffolds

Exemplary properties of a scaffold for use in tissue engineering include at least one of the following: (i) Biocompatibility. After implantation, the scaffold or tissue engineered construct does not elicit an immune response or elicits a negligible immune reaction. (ii) Biogradability. A biodegradable scaffold allows for regeneration of tissue at the site of the implant. (iii) Mechanical properties. The scaffold has mechanical properties consistent with the anatomical site into which it is to be implanted. For example, bone or cartilage scaffold must have sufficient mechanical integrity to function from the time of implantation to the completion of the remodeling process. (iv) Scaffold architecture. Scaffolds may have an interconnected pore structure and/or high porosity.

Three individual groups of biomaterials, i.e., ceramics, synthetic polymers and natural polymers, are commonly used in the fabrication of scaffolds for tissue engineering. Although not generally used for soft tissue regeneration, there has been widespread use of ceramic scaffolds, such as hydroxyapatite (HA) and tricalcium phosphate (TCP), for bone regeneration applications. Ceramic scaffolds are typically characterized by high mechanical stiffness, very low elasticity, and a hard brittle surface. From a bone perspective, they exhibit excellent biocompatibility due to their chemical and structural similarity to the mineral phase of the native bone. The interactions of osteogenic cells with ceramics are important for bone regeneration as ceramics are known to enhance osteoblast differentiation and proliferation.

Numerous synthetic polymers have been used including polystyrene, poly-1-lactic acid (PLLA), polyglycolic acid (PGA) and poly-dl-lactic-co-glycolic acid (PLGA).

The third commonly used approach is the use of biological materials as scaffold biomaterials. Biological materials such as collagen, various proteoglycans, alginate-based substrates and chitosan have all been used in the production of scaffolds for tissue engineering. Unlike synthetic polymer-based scaffolds, natural polymers are biologically active and typically promote excellent cell adhesion and growth. Furthermore the natural polymers are also biodegradable and so allow host cells, over time, to produce their own extracellular matrix.

Collagen and collagen-GAG (CG) scaffolds may be altered through physical and chemical cross-linking. Collagen-hydroxyapatite (CHA) scaffolds, collagen-hydroxy apitite (CHA) scaffolds may be useful for bone defects. Suitable biocompatible materials for the polymers include but are not limited to polyacetic or polyglycolic acid and derivatives thereof, polyorthoesters, polyesters, polyurethanes, polyamino acids such as polylysine, lactic/glycolic acid copolymers, polyanhydrides and ion exchange resins such as sulfonated polytetrafluorethylene, polydimethyl siloxanes (silicone rubber) or combinations thereof.

In one embodiment, the scaffold polymer is formed from natural proteins or materials which may be crosslinked using a crosslinking agent such as 1-ethyl-3-(3-dimethylaminopropyl)carbodiimide hydrochloride. Such natural materials include albumin, collagen, fibrin, alginate, extracellular matrix (ECM), e.g., xenogeneic ECM, hyaluronan, chitosan, gelatin, keratin, potato starch hydrolyzed for use in electrophoresis, and agar-agar (agarose), or other "isolated materials". An "isolated" material has been separated from at least one contaminant structure with which it is normally associated in its natural state such as in an organism or in an in vitro cultured cell population.

Other biocompatible materials include synthetic polymers in the form of hydrogels or other porous materials, e.g., permeable configurations or morphologies, such as polyvinyl alcohol, polyvinylpyrrolidone and polyacrylamide, polyethylene oxide, poly(2-hydroxyethyl methacrylate); natural polymers such as gums and starches; synthetic elastomers such as silicone rubber, polyurethane rubber; and natural rubbers, and include poly[α(4-aminobutyl)]-1-glycolic acid, polyethylene oxide (Roy et al., 2003), polyorthoesters (Heller et al., 2002), silk-elastin-like polymers (Megeld et al., 2002), alginate (Wee et al., 1998), EVAc (poly(ethylene-co-vinyl acetate), microspheres such as poly (D, L-lactide-co-glycolide) copolymer and poly (L-lactide), poly(N-isopropylacrylamide)-b-poly(D,L-lactide), a soy matrix such as one cross-linked with glyoxal and reinforced with a bioactive filler, e.g., hydroxylapatite, poly(epsilon-caprolactone)-poly (ethylene glycol) copolymers, poly(acryloyl hydroxyethyl) starch, polylysine-polyethylene glycol, an agarose hydrogel, or a lipid microtubule-hydrogel.

In one embodiment, complexes are embedded in or applied to a material including but not limited to hydrogels of poloxamers, polyacrylamide, poly(2-hydroxyethyl methacrylate), carboxyvinyl-polymers (e.g., Carbopol 934, Goodrich Chemical Co.), cellulose derivatives, e.g., methylcellulose, cellulose acetate and hydroxypropyl cellulose, polyvinyl pyrrolidone or polyvinyl alcohols, or combinations thereof.

In some embodiments, a biocompatible polymeric material is derived from a biodegradable polymeric such as collagen, e.g., hydroxylated collagen, fibrin, polylactic-polyglycolic acid, or a polyanhydride. Other examples include, without limitation, any biocompatible polymer, whether hydrophilic, hydrophobic, or amphiphilic, such as ethylene vinyl acetate copolymer (EVA), polymethyl methacrylate, polyamides, polycarbonates, polyesters, polyethylene, polypropylenes, polystyrenes, polyvinyl chloride, polytetrafluoroethylene, N-isopropylacrylamide copolymers, poly(ethylene oxide)/poly(propylene oxide) block copolymers, poly(ethylene glycol)/poly(D,L-lactide-co-glycolide) block copolymers, polyglycolide, polylactides (PLLA or PDLA), poly(caprolactone) (PCL), or poly(dioxanone) (PPS).

In another embodiment, the biocompatible material includes polyethyleneterephalate, polytetrafluoroethylene, copolymer of polyethylene oxide and polypropylene oxide, a combination of polyglycolic acid and polyhydroxyalkanoate, gelatin, alginate, poly-3-hydroxybutyrate, poly-4-hydroxybutyrate, and polyhydroxyoctanoate, and polyacrylonitrilepolyvinylchlorides.

In one embodiment, the following polymers may be employed, e.g., natural polymers such as starch, chitin, glycosaminoglycans, e.g., hyaluronic acid, dermatan sulfate and chrondrotin sulfate, and microbial polyesters, e.g., hydroxyalkanoates such as hydroxyvalerate and hydroxybutyrate copolymers, and synthetic polymers, e.g., poly (orthoesters) and polyanhydrides, and including homo and copolymers of glycolide and lactides (e.g., poly(L-lactide, poly(L-lactide-co-D,L-lactide), poly(L-lactide-co-glycolide, polyglycolide and poly(D,L-lactide), pol(D,L-lactide-coglycolide), poly(lactic acid colysine) and polycaprolactone.

In one embodiment, the biocompatible material for the distinct polymer is derived from isolated extracellular matrix (ECM). ECM may be isolated from endothelial layers of various cell populations, tissues and/or organs, e.g., any organ or tissue source including the dermis of the skin, liver, alimentary, respiratory, intestinal, urinary or genital tracks of a warm blooded vertebrate. ECM employed in the invention may be from a combination of sources. Isolated ECM may be prepared as a sheet, in particulate form, gel form and the like.

The biocompatible scaffold polymer may comprise silk, elastin, chitin, chitosan, poly(d-hydroxy acid), poly(anhydrides), or poly(orthoesters). More particularly, the biocompatible polymer may be formed polyethylene glycol, poly (lactic acid), poly(glycolic acid), copolymers of lactic and glycolic acid, copolymers of lactic and glycolic acid with polyethylene glycol, poly(E-caprolactone), poly(3-hydroxybutyrate), poly(p-dioxanone), polypropylene fumarate, poly (orthoesters), polyol/diketene acetals addition polymers, poly(sebacic anhydride) (PSA), poly(carboxybiscarboxyphenoxyphenoxy hexone (PCPP) poly[bis (p-carboxypheonoxy) methane] (PCPM), copolymers of SA, CPP and CPM, poly(amino acids), poly(pseudo amino acids), polyphosphazenes, derivatives of poly[(dichloro)phosphazenes] or poly[(organo) phosphazenes], poly-hydroxybutyric acid, or S-caproic acid, polylactide-co-glycolide, polylactic acid, polyethylene glycol, cellulose, oxidized cellulose, alginate, gelatin or derivatives thereof.

Thus, the polymer employed as a scaffold may be formed of any of a wide range materials including polymers, including naturally occurring polymers, synthetic polymers, or a combination thereof. In one embodiment, the scaffold comprises biodegradable polymers. In one embodiment, a naturally occurring biodegradable polymer may be modified to provide for a synthetic biodegradable polymer derived from the naturally occurring polymer. In one embodiment, the polymer is a poly(lactic acid) ("PLA") or poly(lactic-co-glycolic acid) ("PLGA"). In one embodiment, the scaffold polymer includes but is not limited to alginate, chitosan, poly(2-hydroxyethylmethacrylate), xyloglucan, co-polymers of 2-methacryloyloxyethyl phosphorylcholine, poly (vinyl alcohol), silicone, hydrophobic polyesters and hydrophilic polyester, poly(lactide-co-glycolide), N-isoproylacrylamide copolymers, poly(ethylene oxide)/poly(propylene oxide), polylactic acid, poly(orthoesters), polyanhydrides, polyurethanes, copolymers of 2-hydroxyethylmethacrylate and sodium methacrylate, phosphorylcholine, cyclodextrins, polysulfone and polyvinylpyrrolidine, starch, poly-D,L-lactic acid-para-dioxanone-polyethylene glycol block copolymer, polypropylene, poly (ethylene terephthalate), poly(tetrafluoroethylene), poly-epsilon-caprolactone, or crosslinked chitosan hydrogels.

Exemplary Compositions

In one embodiment, the cmRNA is complexed with or encapsulated in cationic liposomes, cationic emulsions, DOTP, DOTMA, DMRIE, DOSPA, DSPC, DOPE, or DC-cholesterol, which complexes or particles are in a scaffold comprising collagen, bone allograft material, e.g., freeze dried bone allograft, demineralized freeze dried bone allograft, xenograft material, hydroxyapatite, beta-tricalcium phosphate, chitosan, hydrogel, PLGA or alginate, which are optionally modified to include peptides mimicking fibronectin, collagen, arginine-glycine-aspartic acid (RGD), or self-assembling peptides.

In one embodiment, the cmRNA is complexed with or encapsulated in lipofectamine, which complexes or particles are in a scaffold comprising collagen, bone allograft material, e.g., freeze dried bone allograft, demineralized freeze dried bone allograft, xenograft material, hydroxyapatite, beta-tricalcium phosphate, chitosan, hydrogel, PLGA or alginate, which are optionally modified to include peptides mimicking fibronectin, collagen, arginine-glycine-aspartic acid (RGD), or self-assembling peptides.

In one embodiment, the cmRNA is complexed with or encapsulated in peptide based vehicles such as poly-L-lysine or protamine, which complexes or particles are in a scaffold comprising collagen, bone allograft material, e.g., freeze dried bone allograft, demineralized freeze dried bone allograft, xenograft material, hydroxyapatite, beta-tricalcium phosphate, chitosan, hydrogel, PLGA or alginate, which are optionally modified to include peptides mimicking fibronectin, collagen, arginine-glycine-aspartic acid (RGD), or self-assembling peptides.

In one embodiment, the cmRNA is complexed with or encapsulated in, PLGA, PLA, linear or branched PEI of one or different combinations of molecular weights, or dendrimers, e.g., PAMAM, which complexes or particles are in a scaffold comprising collagen, bone allograft material, e.g., freeze dried bone allograft, demineralized freeze dried bone allograft, xenograft material, hydroxyapatite, beta-tricalcium phosphate, chitosan, hydrogel, PLGA or alginate, which are optionally modified to include peptides mimicking fibronectin, collagen, arginine-glycine-aspartic acid (RGD), or self-assembling peptides.

In one embodiment, chemically modified versions of BMP-2-encoding mRNA are transcribed. For example, one version involves the substitution of 25% of uridine and cytidine in the mRNA sequence with 2-thiouridine-5'-triphosphate and 5-methylcytidine-5'-triphosphate (s2U (0.25)m5C(0.25)), respectively, whilst the other version involves the substitution of 100% of uridine and cytidine with pseudouridine-5'-triphosphate and 5-methylcytidine-5'-triphosphate ($\Psi(1.0)$m5C(1.0)), respectively. As described below, initially, both modified mRNA types are compared with the unmodified mRNA for their ability to induce an innate immune inflammatory response as defined by the production of interferon-$\alpha$ (IFN-$\alpha$) in mice. The mRNA modified using $\Psi(1.0)$m5C(1.0) substitutions did not induce IFN-$\alpha$ production. This modified mRNA was then complexed with PEI and used to transfect bone marrow stromal cells (BMSCs) in vitro, which revealed its superior transfection efficacy compared to PEI-pCMV6-XL4[bmp-2] (PEI-pDNA) complexes. In addition, the osteogenic potential of BMSCs treated with these complexes was determined by expression of bone-specific genes, osteocalcin and alkaline phosphatase genes, as well as through the detection of bone matrix deposition. The expression levels of osteocalcin and alkaline phosphatase mRNA were higher, albeit not significantly, in cells transfected with PEI-cmRNA complexes, compared to PEI-pDNA complexes. Von kossa staining demonstrated enhanced osteogenic differentiation as evidenced by increased bone matrix production by BMSCs transfected with PEI-cmRNA complexes.

As described below, the in vivo functional potency of collagen scaffolds loaded with either PEI-cmRNA complexes or PEI-pDNA complexes was evaluated using a calvarial bone defect (CBD) model in rats. Micro-computed tomography ($\mu$CT) scans revealed higher bone formation in the CBDs treated with the collagen scaffold containing PEI-cmRNA complexes, compared to other groups tested. The amount of bone tissue regenerated was quantified by analyzing the trabecular bone volume as a fraction of the total tissue volume of interest (BV/TV) and the degree of trabecular connectivity density. The BV/TV was 5.15-fold and 3.49-fold higher in defects treated with PEI-cmRNA and PEI-pDNA complex-embedded scaffolds, respectively, when compared to the empty defect control groups. Compared to the empty defect control group, the connectivity density of the regenerated bone was 13.67-fold and 7.04-fold greater for the PEI-cmRNA and PEI-pDNA complex-embedded scaffolds, respectively. Evaluation of bone regeneration using histological images further validated the $\mu$CT results. For the PEI-cmRNA complex-embedded scaffolds, complete bridging of the defect by the mature, mineralized bone tissue was observed, while the PEI-pDNA complex-embedded scaffolds promoted mostly soft tissue regeneration with only small edges of new bone formation. In contrast, the untreated defect remained unfilled.

The invention will be described by the following non-limiting examples.

Example 1

The delivery system disclosed herein may overcome most of the barriers of protein—as well as DNA-based therapeutics. Employing biomaterials to embed and release chemically modified ribonucleic acid (cmRNA) in a controlled manner addresses the high cost and safety concerns that exist with recombinant protein and viral based approaches. By eliminating the need for nuclear trafficking (the ultimate barrier for successful transfection in non-dividing cells), cmRNA delivery may address the lower transfection efficiencies associated with other non-viral gene delivery systems and, since this strategy employs non-viral vectors, it alleviates the immunogenic concern that exists with viral vectors. Furthermore, the in vivo approach rather than ex vivo transfection may further reduce the cost (Evans, 2012). Previous murine studies demonstrated the safety and efficacy of the cmRNA-based therapeutics to treat lethal lung disease or to prevent allergic asthma in vivo (Kormann et al., 2011). The present study demonstrates the tissue regenerative potential of cmRNA-based therapeutics. Specifically, complexes of cmRNA and polyethylenimine (PEI) were embedded into collagen matrices which, upon implantation into rat calvarial defects, resulted in enhanced bone regeneration.

Materials and Methods

Materials:

Branched PEI (mol. wt. 25 kDa), the GenElute™ HP endotoxin-free plasmid maxiprep kit and sodium thiosulfate were obtained from Sigma-Aldrich® (St. Louis, Mo.). The BMP-2 ELISA kit was purchased from Quantikine® (R & D Systems®, Minneapolis, Minn.). Plasmid DNA (6.9 Kb) encoding BMP-2 protein driven by cytomegalovirus promoter/enhancer was obtained from Origene Technologies, Inc. (Rockville, Md.). The RNA-easy kit was purchased from Qiagen Inc. The TaqMan Reverse Transcription Reagents and 18S-rRNA were purchased from Applied Biosystems (Foster City, Calif.). Absorbable type-I bovine collagen was obtained from Zimmer Dental Inc. (Carlsbad, Calif.). Human bone marrow stromal cells (BMSCs) were purchased from American Type Culture Collection (ATCC®, Manassas, Va.). Dulbecco's modified eagle medium (DMEM), trypsin-EDTA (0.25%, 1× solution) and Dulbecco's phosphate buffered saline (PBS) were purchased from Gibco® (Invitrogen™, Grand Island, N.Y.). Fetal bovine serum (FBS) was obtained from Atlanta Biologicals® (Lawrenceville, Ga.). Gentamycin sulfate (50 mg/ml) was purchased from Mediatech Inc. (Manassas, Va.). All other chemicals and solvents used were of reagent grade.

Preparation of cmRNA Encoding BMP-2:

To generate templates for in vitro transcription, BMP-2 cDNA was cut out of its original vector and subcloned into a PolyA-120 containing T7 pVAX1 (Life Technologies, Madison, Wis.). Plasmids were linearized with XbaI, following which, its purity was verified and quantified spectrophotometrically. Using MEGAscript T7 Transcription Kits (Life Technologies, Madison, Wis.) mRNA of BMP-2 was synthesized and capped with the anti-reverse cap analog (ARCA; 7-methyl (3'-O-methyl) GpppGm7G (5')ppp(5')G). To achieve mRNA modification, the following modified ribonucleic acid triphosphates were added to the reaction at a ratio of 25%:2-thiouridine-5'-triphosphate and 5-methyl-cytidine-5'-triphosphate (s2U(0.25)m5C(0.25)) as well as pseudouridine-5'-triphosphate and 5-methylcytidine-5'-triphosphate ($\Psi$(1.0)m5C(1.0)) at a ratio of 100%. Synthesized mRNA was purified and analyzed for size and purity. Once the cmRNA of BMP-2 was synthesized, the degree of immune response to cmRNA was evaluated. Unmodified mRNA and cmRNA of BMP-2 were injected into the peritoneum of BALB/c mice and serum levels of IFN-α (R&D systems, Minneapolis, Minn.) were measured by ELISA, 24 hours post-injection.

Preparation of pDNA Encoding BMP-2:

The chemically competent DH5α™ bacterial strain (*Escherichia coli* species) was transformed with pDNA to amplify the plasmid. The pDNA in the transformed cultures was then expanded in *E. coli* in Lennox L Broth (LB Broth) overnight at 37° C. in an incubator shaker at 300 rpm. Plasmid DNA was extracted using GenElute™ HP endotoxin-free plasmid maxiprep kit and was analyzed for purity using a NanoDrop 2000 UV-Vis Spectrophotometer (Thermoscientific, Wilmington, Del.) by measuring the ratio of absorbance ($A_{260}/A_{280}$ nm). The concentration of pDNA solution was determined by absorbance at 260 nm.

Fabrication of PEI-pDNA and PEI-cmRNA Polyplexes:

PEI-pDNA polyplexes were prepared by adding 50 μL PEI solution to 50 μL pDNA (BMP-2) solution containing 25 μg pDNA and mixed by vortexing for 30 seconds. The mixture was incubated at room temperature for 30 minutes to allow complex formation between the positively charged PEI (amine groups) and the negatively charged pDNA (phosphate groups). To achieve optimal transfection efficacies, polyplexes were fabricated using N (nitrogen) to P (phosphate) ratios (molar ratio of amine groups of PEI to phosphate groups in pDNA backbone) of 10 (Elangovan et al., 2014). Similarly, PEI-cmRNA polyplexes at N/P of 10 were synthesized by mixing 50 μL, of PEI solution to 50 μL, cmRNA encoding BMP-2 containing various amounts of cmRNA for 30 seconds. For in vitro transfection experiments, we utilized PEI-cmRNA polyplexes containing final amounts of 0.2, 0.72 or 1.2 μg of cmRNA (BMP-2). For in vivo testing we prepared polyplexes containing final amounts of 25 μg of cmRNA (BMP-2) that was then added to the collagen scaffolds, prior to implantation.

In Vitro Evaluation of Cytotoxicity of PEI-pDNA and PEI-cmRNA Polyplexes at a N/P Ratio of 10 in BMSCs:

Cytotoxicity of PEI-pDNA and PEI-cmRNA polyplexes on BMSCs, at an N/P ratio of 10 was evaluated using an MTS cell growth assay (Cell Titer 96 AQueous One Solution cell proliferation assay, Promega Corporation). Cells were seeded at a density of 10,000 cells/well in clear polystyrene, flat bottomed, 96-well tissue culture grade plates (Costar®, Corning Inc.) and allowed to attach overnight. The next day, at a cell confluence about 80%, the cell culture medium was changed to serum-free medium and the treatments were gently mixed and added drop-wise into the wells. Each well was treated with 20 μL of polyplexes containing 1 μg of pDNA or cmRNA. Untreated BMSCs were used as controls. Cells treated with PEI alone served as additional controls. To mimic the conditions used in the transfection experiments, the polyplexes were incubated with the cells for 4 hours. At the end of the incubation period, the cells were washed with 1×PBS and fresh complete medium was added. After a total incubation time of 48 hours, cells were washed with 1×PBS and fresh complete medium was added to the cells followed by addition of 20 μL MTS (3-(4,5-dimethylthiazol-2-yl)-5-(3-carboxymethoxyphenyl)-2-(4-sulfophenyl)-2H-tetrazolium) cell growth assay reagent. The plates were then incubated at 37° C. in a humidified 5% $CO_2$ atmosphere for 3 hours. The amount of soluble formazan produced by reduction of MTS reagent by viable cells was measured spectrophotometrically using SpectraMax® Plus384 (Molecular Devices, Sunnyvale, Calif.) at 490 nm. The cell viability was expressed by the following equation: cell viability (%)=(absorbance intensity of treated cells/absorbance intensity of untreated cells (control))×100. Values are expressed as mean±SD and each treatment was performed in quadruplicate.

In Vitro Evaluation of Transfection of BMSCs with PEI-pDNA and PEI-cmRNA Polyplexes:

The bone marrow stromal cells (BMSCs) were plated in 24-well plates at a seeding density of $8 \times 10^4$ cells/well 24 hours prior to treatments. BMSCs were treated with the PEI-pDNA polyplexes containing 1 μg pDNA and the PEI-cmRNA polyplexes containing 0.2, 0.75 and 1.20 μg of cmRNA encoding BMP-2 all synthesized at a N/P of 10 for 4 hours at 37° C. and then followed by a subsequent wash with PBS (1×). After a total incubation time of 48 h, BMSCs were treated with heparin (10 mg/mL) for 4 hours to prevent BMP-2 protein retention on the BMSC surface. The cell culture supernatants were assayed for BMP-2 protein levels using an ELISA kit. Untreated cells were employed as controls. The mean value was recorded as the average of four measurements.

2.7. Real-Time PCR (RT-PCR) Analysis:

Osteoblast genotypic markers tested were osteocalcin and alkaline phosphatase. On day 3 post-transfection, total RNA was extracted from BMSCs using RNeasy kit (Qiagen Inc, Valencia, Calif.). RNA extracts were normalized for PCR analysis using a spectrophotometer at 260 nm. Complementary DNA (cDNA) was generated by reverse transcription of the normalized RNA and was amplified using TaqMan Reverse Transcription Reagents. cDNA samples (3 μL for a total volume of 75 μL per reaction) were analyzed both for targeted osteogenic genes, as well as 18S-rRNA as a control (Undisclosed sequences, Applied Biosystems, Foster City, Calif.). Real-time PCR reactions were performed in 96-well Optical Reaction Plates (Applied Biosystems, Foster City, Calif.), using a 7300 real-time PCR system (Applied Biosystems, Foster City, Calif.).

Von-Kossa Staining:

The osteogenic differentiation of BMSCs was studied after 14 days of receiving the various treatments using Von-Kossa staining. The cell cultures were washed with PBS (1×) and fixed in 4% paraformaldehyde (Alfa Aesar, Ward Hill, Mass.) for 30 min. Then cells were washed with water, and a 5% silver nitrate solution (Fisher Scientific, Pittsburgh, Pa.) was added and the plate was exposed to UV for 40 min, after which the plate was rinsed with water several times. Sodium thiosulfate (5%) (Sigma-Aldrich) was added for 5 min and then the plate was rinsed in water and 1% Nuclear Fast Red solution (Rowley Biochemical Institute, Danvers, Mass.) was added for 5 min. The plate was washed with water, followed by dehydration with ethanol, and dried for imaging. The cells were imaged with the Nikon TE-300 inverted microscope.

Alizarin Red Staining:

In addition to Von-Kossa staining, the calcium deposition by BMSCs was assessed using Alizarin red staining. After 14 days, the cell cultures were washed with PBS (1×) for 5 minutes and fixed in 10% formalin (Alfa Aesar, Ward Hill, Mass.) for 10 minutes. Then cells were washed with water, and 2% Alizarin red S at a pH range of 4.1-4.3 (Sigma-Aldrich,) was added to the wells for 10 minutes. Then the plate was rinsed with distilled water several times until no additional Alizarin red continued to seep into the solution, and was then dried for imaging. The cells were imaged with the Nikon TE-300 inverted microscope.

Atomic Absorption Spectroscopy:

Released $Ca^{2+}$ ions from BMSCs were measured with a flame atomic absorption spectrophotometer (Perkin Elmer Model 2380). Cells were acid hydrolyzed 14 days post transfection using 0.6 N HCL overnight. Samples were prepared by combining 450 μL of acid hydrolyzed samples with 550 μL of 2.5% $La_2O_3$ in 0.6 N HCl. The samples were measured at 422.7 nm with a Perkin Elmer intenistron calcium lamp, a slit of 0.7 nm, and energy of 49 keV. The instrument was calibrated using commercial calcium standards. Calcium standards were prepared by dissolving 20 ppm calcium stock in required volumes of solution containing 0.6 N HCl in 1×PBS and 2.5% lanthanum oxide.

In Vivo Implantation of Complex Embedded Collagen Scaffolds:

Fisher (CDR)) male white rats (F344/DuCrl, 14 weeks old, 250 g) were purchased from Harlan Laboratories (Indianapolis, Ind.) and housed and cared for in the animal facilities. All animal protocols used in these studies were approved by and performed according to guidelines established by the University of Iowa Institutional Animal Care and Use Committee, Iowa. The animals were anaesthetized by intra-peritoneal injection of the mixture of ketamine (80 mg/kg) and xylazine (8 mg/kg). Following a sagittal incision in the scalp, the soft tissues were reflected using blunt dissection to expose the calvarium. Using a round carbide bur, two specific-sized defects (5 mm diameter×2 mm thickness) were generated on the parietal bone, on both sides of the sagittal suture. The four groups employed in this study were: 1) empty defect (n=7); 2) defect implanted with PEI loaded collagen scaffold (n=7); 3) defect treated with PEI-pDNA complex-loaded collagen scaffold (n=7); and 4) defect treated with PEI-cmRNA complex-loaded collagen scaffold (n=7). Where applicable, the scaffold was cut into cylinders with a diameter of 5 mm and a thickness of 2 mm and the solution, containing PEI complexes, was injected into each scaffold which was then implanted into the rats. Next, using sterile silk sutures the incision was closed and buprenorphine (0.15 mg), was administered intramuscularly for pain management. Rats were euthanized after 4 weeks, the regions of interest were cut from the calvarial bone, dissected and fixed in neutral buffered formalin (10%) for analyses.

Micro-Computed Tomography (μCT) Analysis:

To quantitatively measure the amount of bone formed, three-dimensional x-ray micro-computed tomography (μCT) imaging was performed. A cone-beam μCT system (μCT 40, Scanco Medical AG, Switzerland) was utilized to scan the specimens in 70% ethanol at a source voltage of 55 kVp and beam current of 145 μA with a voxel size of 10 μm and an integration time of 300 milliseconds. The region of interest analyzed consisted of a constant 3.5 mm diameter circular region that was placed in the center of the machined defect and spanned a total of 50 reconstructed slices. Using the manufacturer's software (sigma=0.8, support=1.0, and threshold=250) approximately 3.8 $mm^3$ (oriented perpendicular to the outer table of the calvarium) of each defect in the specimen was analyzed. Bone volume (BV) per total volume (TV) and connectivity density parameters were calculated using the μCT software.

Histological Observation of Rat Bone Samples:

After completing the μCT, the specimens (empty defect, PEI-pDNA complex-loaded scaffolds, and PEI-cmRNA complex-loaded scaffolds) were decalcified using a Surgipath Decalcifier II procedure. The specimens were embedded in paraffin after dehydration in ascending concentrations of ethanol, followed by treatment with xylene (Merck, Germany). Histological sections (5 µm) in the central portion of the wound were prepared in the sagittal plane and collected on Superfrost Plus Slides (Fisher Scientific, Pittsburgh, Pa.). Sections were deparaffinized and stained with Hematoxylin-Eosin (H & E staining) according to standard protocols. To evaluate in vivo bone regeneration after 4 weeks; six sections, representing the central area of each defect, including intact native bone margins surrounding the reconstructed defects, were used to assess new bone formation and bridging of the created defect. The Olympus Stereoscope SZX12 and an Olympus BX61 microscope, both equipped with a digital camera, were utilized for the bright field examination of the slides.

Statistical Analysis:

Numerical data are represented as mean (±SD). All statistical analyses were performed using statistical and graphing software, GraphPad Prism version 5.02 for windows (GraphPad Software Inc., San Diego, Calif.). Unless otherwise stated the following stats were used; treatment groups were compared using Kruskal-Wallis and one-way analysis of variance followed by Dunnett's post-test analysis comparing all pairs of treatments. Differences were considered significant at p-values that were less than or equal to 0.05.

Results and Discussion

This report investigates the safety and efficacy of cmRNA activated matrix in bone regeneration in rats. This form of RNA activated matrix provides localized transient protein therapy, since the nuclear translocation (the rate limiting step in gene therapy) is not required with this strategy. Compounds having cmRNA were synthesized and thoroughly characterized, e.g., cmRNA (BMP-2) alone, the PEI-cmRNA (BMP-2) polyplexes alone and also after embedding them in the collagen scaffold. Using appropriate controls, it was further demonstrated the in vivo bone regeneration capacity of this novel RNA activated matrix in rat calvarial bone defect (CBD).

Generation of cmRNA and pDNA Encoding BMP-2 Proteins

Two chemically modified versions of BMP-2-encoding mRNA were transcribed (FIG. 1a). One version involved the substitution of 25% of uridine and cytidine in the mRNA sequence with 2-thiouridine-5'-triphosphate and 5-methylcytidine-5'-triphosphate (s2U(0.25)m5C(0.25)), respectively, whilst the other version involved the substitution of 100% of uridine and cytidine with pseudouridine-5'-triphosphate and 5-methylcytidine-5'-triphosphate ($\Psi(1.0)$m5C (1.0)), respectively. Initially, both modified mRNA sequences were compared with the unmodified mRNA for their ability to induce an innate immune inflammatory response as defined by the production of interferon-$\alpha$ (IFN-$\alpha$) in mice. As desired, the mRNA modified using $\Psi(1.0)$ m5C(1.0) substitutions did not induce IFN-$\alpha$ production (Kormann et al., 2011; Kariko et al., 2004), and was therefore used in subsequent experiments (FIG. 1b).

Morphology, Size and Surface Charge of PEI-cmRNA Polyplexes

Figure 2:
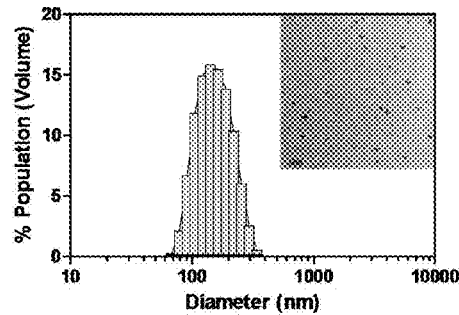
FIG. 2. Representative PEI-cmRNA polyplexes (N/P ratio 10) size distribution diagram as determined using Zetasizer Nano (inset: TEM image with scale bar=0.2 μm).

The cmRNA prepared above was then complexed with PEI through electrostatic condensation. The PEI-cmRNA polyplexes size, charge, and morphology at a N/P ratio of 10 were assessed using a Zetasizer Nano-ZS and transmission electron microscopy (TEM). The polyplexes were 153 nm (±2 nm) in diameter with a net surface charge of +37.7 mV (FIG. 2). The polyplexes had narrow size distributions with the average polydispersity index (PDI) equal to 0.1. The inset of FIG. 2 shows a TEM image of the polyplexes, demonstrating spherical polyplexes with monomodal distribution. The small size as well as the positive surface charge of the polyplexes contribute to efficient in vitro cellular uptake by clathrin-mediated endocytosis (Wagner et al., 1991) as well as in vivo distribution and diffusion (Ferkoll et al., 1995 in the target tissues.

In Vitro Cell Viability Assay for PEI-pDNA and PEI-cmRNA Polyplexes

Figure 3:
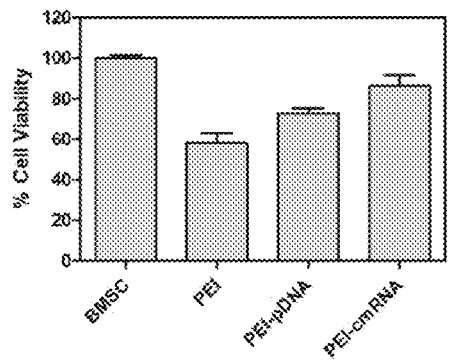
FIG. 3. MTS assay assessing the cytotoxicity of PEI-pDNA and PEI-cmRNA polyplexes in BMSCs after 48 hours. Significant differences between the treatments and the untreated cells were assessed by one-way analysis of variance followed by Tukey's post-test (***$p<0.001$). Values are expressed as mean±SD (n=4).

The cytotoxicity of polyplexes, containing 1 µg of pDNA or cmRNA, at a N/P ratio of 10 was evaluated over 48 h using a MTS assay. FIG. 3 demonstrates that BMSCs viabilities were approximately 75% and 85% when transfected with PEI-pDNA and PEI-cmRNA polyplexes, respectively. Although the trend toward greater viabilities for BMSCs treated with PEI-cmRNA versus PEI-pDNA was not statistically significant, it was, however, noted that the decrease in cell viability for BMSCs treated with PEI-pDNA compared to untreated BMSCs was statistically significant (***$p<0.001$). The difference in cell viabilities between untreated BMSCs and PEI-cmRNA treated BMSCs was not significant. These data suggest that PEI-cmRNA polyplexes may have an advantage over PEI-pDNA polyplexes in terms of maintaining higher cell viabilities.

In Vitro Investigation of Gene Expression by PEI-pDNA and PEI-cmRNA Polyplexes

Figure 4:
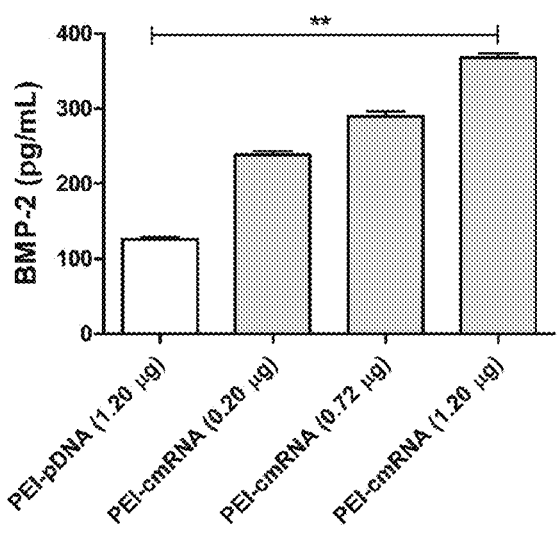
FIG. 4. ELISA assay demonstrating BMP-2 secretion from BMSCs at 48 hours after transfection with PEI-cmRNA and PEI-pDNA polyplexes (prepared at a N/P ratio of 10 (1.2 μg cmRNA)). Significant differences between PEI-pDNA and PEI-cmRNA (1.20 μg) were assessed by Kruskal-Wallis nonparametric test followed by Dunns post-test (**$p<0.01$). Values are expressed as mean±SD (n=4).

The ability of the synthesized PEI-pDNA and PEI-cmRNA polyplexes to transfect BMSCs was evaluated through expression of BMP-2. BMPs are potent morphogens that belong to the transforming growth factor beta (TGF-$\beta$) super family and are known for their ability to induce ectopic bone formation, maintain post-natal skeletal homeostasis and to play a role in bone regeneration (Rosen, 2009). BMP-2 is an osteogenic factor which initiates bone formation and healing (Sakou, 1998) while inducing the expression of other BMPs (Sandberg et al., 1993). As demonstrated in FIG. 4, BMSCs transfected with PEI-cmRNA polyplexes resulted in significantly higher levels of BMP-2 compared to cells treated with PEI-pDNA polyplexes (p value=0.0011, Kruskal-Wallis test). After transfection of cells with PEI-cmRNA, BMP-2 was secreted into the cell culture supernatant at concentrations approximately 3 times higher than cells treated with the PEI-pDNA. Furthermore, in the BMSCs treated with PEI-cmRNA polyplexes dose-titratable expression of BMP-2 was observed which is known as one of the modified-mRNA technology properties that make it a powerful platform for directing cell fate (Mandal and Rossi, 2013). These results revealed superior transfection efficiency of the cmRNA complexed with PEI, compared to PEI-pDNA polyplexes.

Figure 5:
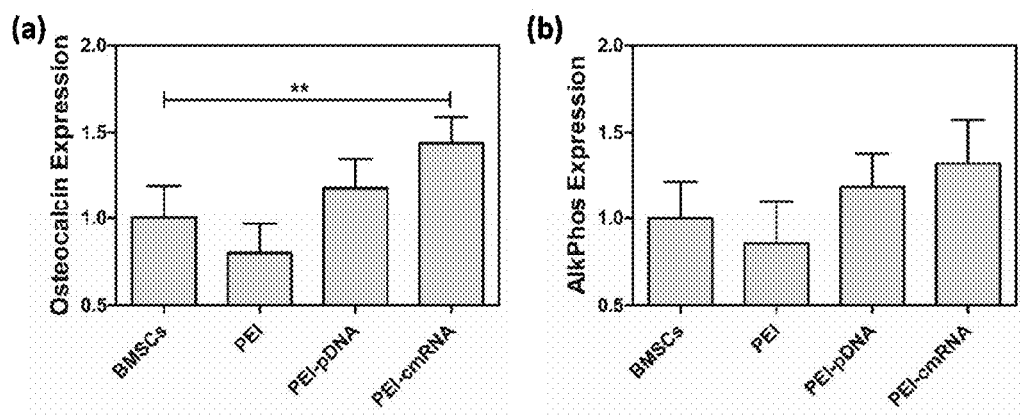
FIG. 5. (a) Osteocalcin and (b) alkaline phosphatase mRNA levels in BMSCs were determined using real-time PCR analysis, 3 days after treatment with either PEI-cmRNA or PEI-pDNA polyplexes (prepared at a N:P ratio of 10 (1.2 μg cmRNA)) (n=4). Significant differences between the treatments and the untreated controls were assessed by one way ANOVA followed by Dunnett's multiple comparison post-test (**$p<0.01$). Values are expressed as mean±SD.

In Vitro Evaluation of Bone Osteogenic Differentiation of BMSCs Pretreated by PEI-pDNA and PEI-cmRNA Polyplexes The osteogenic potential of BMSCs treated with PEI-pDNA and PEI-cmRNA polyplexes was assessed using real time PCR to measure the levels of transcription of bone-specific genes, osteocalcin (OCN) and alkaline phosphatase (ALP). Cells were transfected with polyplexes prepared at an N/P ratio of 10 and containing 1.2 µg of pDNA (encoding BMP-2) or cmRNA (encoding BMP-2) for 4 hours, followed by further incubation for 3 days. The expression levels of OCN in BMSCs that were pretreated with PEI-cmRNA was significantly higher than the levels detected in controls (P value=0.0013, Dunnett's multiple comparison test). Similarly, ALP levels detected in BMSCs that had been pretreated with PEI-cmRNA were slightly higher, albeit not significantly, compared to the levels detected in controls (FIG. 5). The in vitro levels of bone-specific markers such as ALP and OCN in the differentiated BMSCs are associated with their in vivo bone regenerative capabilities (Mauney et al., 2005), therefore the enhancement of ALP and OCN expression in cells treated with PEI-cmRNA suggests that these cells have higher bone regenerative potential.

Figure 6:
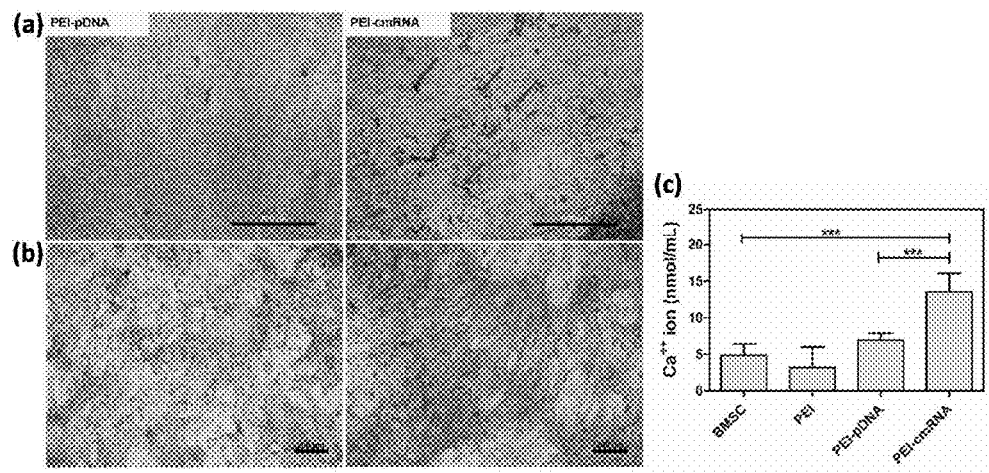
FIG. 6. (a) Von Kossa staining, arrows indicate black precipitations associated with calcium salt (scale bar, 500 μm) (b) Alizarin red (scale bar, 200 μm) staining (c) and atomic absorption performed to detect calcium mineralization produced by BMSCs 14 days after treatment with either PEI-cmRNA or PEI-pDNA polyplexes. Significant differences between the treatments and the untreated cells were assessed by one-way analysis of variance followed by Tukey's post-test (***$p<0.001$). Values are expressed as mean±SD (n=4).

In Vitro Evaluation of Bone Matrix Deposition by Von-Kossa, Alizarin Red Staining and Atomic Absorption Spectroscopy Extracellular matrix calcification was evaluated in the BMSCs transfected with PEI-pDNA and PEI-cmRNA polyplexes after 14 days using qualitative (Von-kossa and Alizarin red staining) and quantitative (atomic adsorption spectroscopy) methods. Qualitative assessment revealed that the cells that had been pretreated with PEI-cmRNA appeared to stain darker, or more intensely, than PEI-pDNA pretreated BMSCs (FIGS. 6a and 6b).

Calcium deposition 14 days post transfection was quantitatively analyzed using an atomic absorption spectrophotometer. Cells transfected with PEI-cmRNA promoted significantly higher levels of calcium deposition compared to untreated cells as well as cells transfected with PEI-pDNA polyplexes (p value <0.0001, Tukey's multiple comparison post-test). In contrast, cells transfected with PEI-pDNA demonstrated only an increase in calcium content compared to the untreated cells that was not statistically significant (FIG. 6c). The results presented here indicate enhanced osteogenic differentiation as evidenced by increased calcium deposition in BMSCs transfected with PEI-cmRNA polyplexes compared to the cells transfected with PEI-pDNA and control.

In Vivo Bone Regeneration

Figure 7:
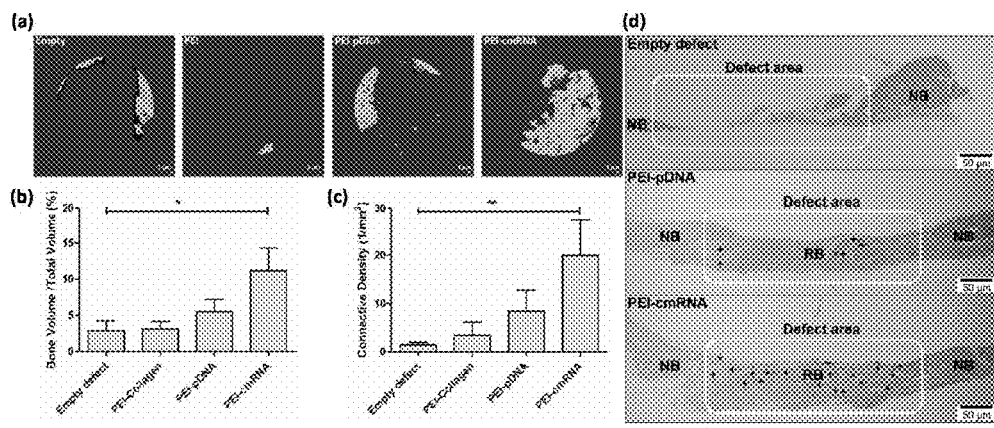
FIG. 7. (a) Representative μCT scans showing the level of regenerated bone tissue after 4 weeks in CBD treated with: empty defects, PEI-treated scaffolds, PEI-pDNA complex-loaded scaffolds, or PEI-cmRNA complex-loaded scaffolds (n=7). (b) Assessment of bone volume fraction and (c) connectivity density of regenerated bone after 4 weeks of implantation. Significant differences between PEI-cmRNA treatments and control group were assessed by Kruskal-Wallis nonparametric test followed by Dunns post-test (**$p<0.01$, *$p<0.1$). (Values are expressed as mean±SD). (d) Illustrative histology sections demonstrating the extent of new bone formation in the defects at 4 weeks due to various treatments. Note the complete bridging of new bone in the group treated with PEI-cmRNA-embedded scaffolds, and partial filling for the group treated with PEI-pDNA-embedded scaffolds. RB-regenerated bone and NB-native bone. Note the bridging of new bone in the PEI-cmRNA complex-loaded test group indicated by the arrows. Scale bar, 50 μm.
Figure 8:
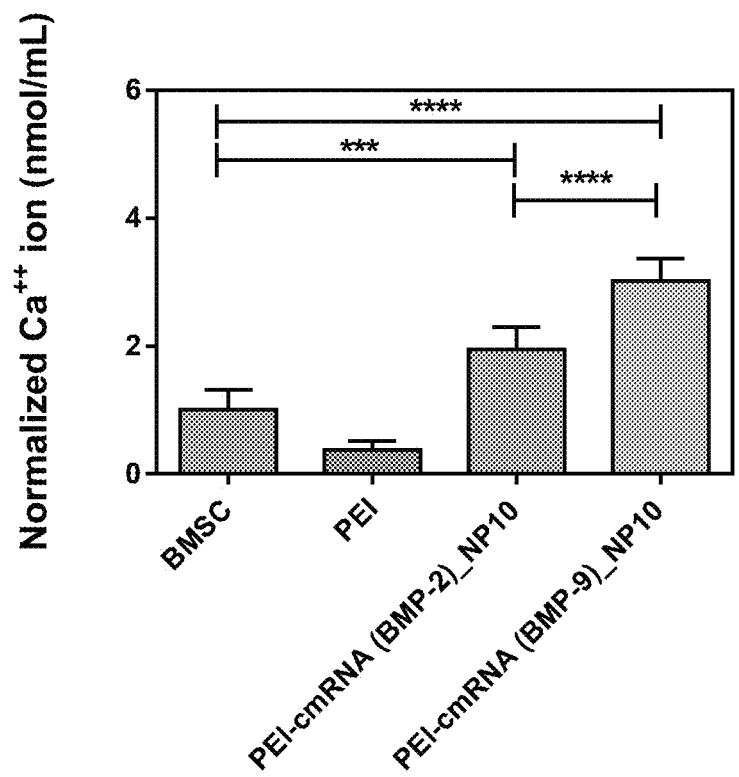
FIG. 8. Atomic absorption was performed to detect calcium deposition induced by BMSCs 14 days after treatment with either PEI-cmRNA encoding BMP-2 versus BMP-9 polyplexes. Significant differences between the treatments and the untreated cells were assessed by one-way analysis of variance followed by Tukey's post-test (****$p<0.0001$). Values are expressed as mean±SD (n=8). The data is normalized to BMSC value as a control. Calcium deposition produced by BMSCs treated with either PEI-cmRNA (BMP- 2) or PEI-cmRNA (BMP-9) was significantly higher, when compared to BMSCs treated with PEI or BMSCs alone.

The functional potency of collagen scaffolds loaded with either PEI-pDNA polyplexes or PEI-cmRNA polyplexes was evaluated in vivo using a CBD model in rats. The in vivo efficacy of the following four treatment groups was evaluated: (1) empty defect, (2) defect implanted with collagen scaffold treated with PEI, (3) defect implanted with PEI-pDNA polyplexes entrapped in collagen scaffold, and (4) defect implanted with PEI-cmRNA polyplexes entrapped in collagen scaffold. After 4 weeks of in vivo implantation of the collagen scaffolds, rats were sacrificed and newly-formed bone tissue was evaluated using Micro-computed tomography (μCT) scans. The μCT scans revealed increased quantities of mineralized bone matrix in the CBDs treated with collagen scaffolds containing PEI-cmRNA polyplexes, compared to other treatment groups (FIG. 7a). The amount of bone tissue regenerated was quantified by analyzing the mineralized bone volume as a fraction of the total tissue volume of interest (BV/TV) and connectivity density of the regenerated bone. The BV/TV was 3.94-fold and 1.94-fold higher in defects treated with PEI-cmRNA and PEI-pDNA complex-embedded scaffolds, respectively, when compared to the empty defect (control) group. The distribution of BV/TV of defects treated with PEI-cmRNA was significantly higher compared to empty defects (p=0.039, Kruskal-Wallis test) (FIG. 7b). Compared to the empty defect control group, the connectivity density of the regenerated bone was 14.07-fold and 5.82-fold greater for the PEI-cmRNA and PEI-pDNA complex-embedded scaffolds, respectively. The difference between connectivity density of the PEI-cmRNA group and the empty defect group was significant (p=0.0028, Kruskal-Wallis test) (FIG. 7c). Evaluation of bone regeneration using histological images further validated the μCT results. For the PEI-cmRNA complex-embedded scaffolds, extensive bridging of the defect by the mature, mineralized bone tissue was observed, while the PEI-pDNA complex-embedded scaffolds promoted mostly soft tissue regeneration with only small amounts of new bone formation at the defect margins. In contrast, the untreated defects remained unfilled (FIG. 7d).

Conclusion

The safety and efficacy of cmRNA based therapeutics in bone regeneration is demonstrated in rats. It's clear that cmRNA encoding BMP-2 (at equivalent dosage) surpassed its pDNA counterpart in both biocompatibility and bone regeneration capacity. As mentioned earlier, cmRNA therapeutics has significant potential to be translated to clinics in both orthopedics and in dentistry, where the need for cost-effective bone replacement grafts is enormous. This study clearly underscores the promising translational potential of this therapeutic strategy for tissue engineering applications, particularly bone regeneration.

Thus, a delivery system is described that has the potential to overcome most of the barriers of protein as well as DNA based therapeutics. Employing inexpensive yet safe biomaterials to embed and release chemically modified ribonucleic acid (cmRNA) in a controlled manner addresses the high cost and safety concerns that exist with recombinant protein and viral based gene therapeutic approaches. By eliminating the need for nuclear trafficking (the ultimate barrier for successful transfection in non-dividing cells), cmRNA delivery would potentially address the lower transfection efficiencies associated with non-viral gene delivery systems and, since this strategy employs non-viral vectors, it alleviates the immunogenic concern that exists with viral vectors as well. Other advantages include a simpler purification process and greater safety, as mRNA does not integrate into the genome. Furthermore, the in vivo approach rather than ex vivo transfection will further reduce the treatment cost significantly. Previous murine studies demonstrated the safety and efficacy of cmRNA-based therapeutics to treat lethal lung disease or to prevent allergic asthma in vivo. The major limitation of using mRNA is the associated immunogenicity, mediated primarily through toll-like receptors (TLR)-3, 7 and 8. However, modifying the nucleotides significantly contributed to a reduction in immunogenicity whilst retaining its function.

Example 2

A system that releases cmRNA of bone morphogenetic protein (BMP-2) in a controlled fashion in order to induce bone regeneration was tested by determining the in vivo efficacy of PLGA-PAMAM-cmRNA (BMP-2) in a rat calvarial defect model. Poly (D, L-lactide-co-glycolide) (PLGA) microspheres incorporating polyamidoamine (PA-MAM)-cmRNA (encoding BMP-2) dendriplexes are synthesized and characterized for size and surface charge. The cytotoxicity and transfection efficiency is evaluated in human bone marrow stromal cells (BMSC) and murine pre-osteoblastic cells (MC3T3-E1). Expression levels of bone specific genes (osteocalcin and type I collagen), core binding factor (Cbfa)-1 and Osterix in transfected cells are determined, while the functionality of transfection is determined by assessing mineral nodule formation and measuring alkaline phosphatase and calcium levels in transfected cells. The preparations are implanted in calvarial defects in Fisher 344 rats, and after four weeks, animals are euthanized. New bone volume and area (%) at the implanted sites are assessed using imaging and histological techniques. The in vivo delivery of cmRNA (encoding BMP-2) into osseous defects will likely promote significant bone regeneration.

Synthesis and Characterization of a Biomaterial-Based cmRNA (BMP-2) Delivery System.

Delivery of genes into cells using cationic polyplexes remains a well-established approach in non-viral gene delivery. Among the polyplexes explored, PAMAM, a non-viral gene delivery vector known for its "proton-sponge" effect and minimal cytotoxicity, is employed as a vector to deliver cmRNA (BMP-2) into BMSC and MC3T3-E1 cells (Haensler and Szoka, 1993). PAMAM has been shown to be effective in transfecting cells even in the presence of serum, a quality desired for in vivo applications (Intra and Salem, 2010). Synthesis of PAMAM-cmRNA (BMP-2) dendriplexes follows the synthesis of cmRNA encoding BMP-2 (Example 1) using in vitro transcription with specific modifications in the bases. The dendriplexes are characterized for size, morphology, polydispersity and surface charge. PAMAM-cmRNA (BMP2) dendriplexes are also characterized for surface properties, size and cmRNA condensation. cmRNA (BMP-2) is tested for its lack of immunogenicity using RNA immunoprecipitation.

PAMAM-cmRNA (BMP-2) dendriplexes are then incorporated into PLGA microspheres. The biocompatibility and transfection efficacy of dendriplexes alone and when incorporated in PLGA microspheres are evaluated. To quantify transfection, the amount of secreted BMP-2 in the media after transfection is determined. Functionality of transfection is determined by assessing bone nodule formation using Alizarin red S staining and by determining alkaline phosphatase (ALP) activity and calcium levels in transfected cells. The functionality of transfection in BMSC and MC3T3-E1 cells with PLGA microspheres incorporating PAMAM-cmRNA (BMP-2) dendriplexes is tested using molecular and calorimetric assays. The in vitro cytotoxicity and transfection efficiency of PAMAM-cmRNA dendriplexes alone and PLGA microspheres containing the dendriplexes are evaluated in BMSC and MC3T3-E1 cells, which have been shown to be a suitable in vitro model cells to study osteogenesis. The osteoblastic differentiation of transfected cells is determined by evaluating the expression of bone specific genes (collagen type I and osteocalcin), core binding factor (Cbfa-1) and Osterix at specific time points, post-treatment.

The entire system is dispersed in collagen matrix prior to its use in in vivo studies.

Synthesis of cmRNA Encoding BMP-2:

In vitro transcription of BMP-2 mRNA is performed using plasmid constructs containing complementary DNA (cDNA) of BMP-2 as the template. This cDNA is flanked upstream by a T7 promoter and downstream by a poly (A) tail of 120 bp in length. Plasmids are first linearized with XbaI, following which purity is verified and quantified spectrophotometrically. Using commercially available high yield transcription kits, mRNA of BMP-2 is synthesized and capped with the anti-reverse cap analog (ARCA; 7-methyl (3'-O-methyl) GpppGm7G (5')ppp(5')G).

To achieve mRNA modification, the following modified ribonucleic acid triphosphates are added to the reaction at a ratio of 10%:2-thiouridine-5'-triphosphate and 5-methylcytidine-5'-triphosphate. Synthesized mRNA is purified and analyzed for size and purity prior to PAMAM-cmRNA (BMP-2) complex formation. Once the cmRNA of BMP-2 is synthesized, the degree of immune response to cmRNA is evaluated. The binding of cmRNA to pattern recognition receptors such as toll-like receptor (TLR) 3, 7 and 8 is determined in peripheral blood mononuclear cells using RNA immunoprecipitation as described in Kormann et al. (2011). Scrambled cmRNA (BMP-2) with altered sequence is also synthesized and used in in vitro and in vivo experiments as a negative control.

Synthesis and Characterization of PAMAM-cmRNA (BMP-2) Dendriplexes and PLGA Microspheres:

PAMAM dendrimers encapsulating cmRNA (BMP-2) with a range (1, 5, 10, 15 and 20) of N/P ratios (ratio of the total number of dendrimer end amine groups and the total number of RNA phosphate groups) are synthesized. The N/P ratio was previously shown to influence the size, surface charge, transfection efficiency, and cytotoxicity of PAMAM dendriplexes (Intra and Salem, 2010). Based on the number of amine groups that are present, PAMAM dendrimers are classified into 7 generations (PG1 to PG7) (Zhan et al., 2006). Pilot studies indicated that synthesized PLGA microspheres incorporating PAMAM-pDNA dendrimers (with an N/P ratio of 5) were in the range of 800 to 1000 nm in diameter (depending on the generation of PAMAM employed) with a surface charge in the range of 8 to 30 Mv. PLGA microspheres incorporating PAMAM dendrimers were significantly less cytotoxic, when exposed to cells for 4 hours (Intra and Salem, 2010). PLGA microspheres incorporating the PAMAM-pDNA dendrimers (encoding firefly luciferase reporter gene) contacted with Human embryonic kidney cells (HEK293) and monkey African green kidney fibroblast-like cell line (COS7), demonstrated significantly higher transfection when PLGA microspheres incorporating the third generation of PAMAM dendrimers (PG3) were used, compared to all the other generations (PG4, PG5 and PG6) tested. These results indicated that apart from N/P ratio, dendrimer generation had an effect on the transfection of the dendriplexes.

After synthesis of PAMAM-cmRNA (BMP-2) dendriplexes, the size and polydispersity of the synthesized dendriplexes are determined using dynamic light scattering and transmission electron microscopy (TEM) analysis of carbon-coated grids coated with preparations for 1 minute and staining them with 1% uranyl acetate. PAMAM dendrimers are known for their spherical, monodisperse features with a reduced structural density in the intra-molecular core (Asfond and Tomaka, 2001). Zeta potential (surface charge) that is based on the electrophoretic mobility of the nano complexes using folded capillary cells is determined using the laser scattering method. Once the physical characteristics are assessed, encapsulation efficiency and cmRNA condensation within the complex is elucidated using spectrophotometric and gel electrophoresis, respectively. PLGA microspheres are then fabricated from the PLGA polymer using double emulsion-solvent evaporation method during which, PAMAM-cmRNA (BMP-2) dendriplexes are incorporated into the microspheres (Intra and Salem, 2010). Scanning electron microscopy (SEM) of PLGA microspheres with and without complexes is performed. SEM of PLGA microspheres synthesized during pilot experiments demonstrated their characteristic size and morphology. Mechanical integrity and rheological properties of the delivery system is analyzed by measuring the tensile strength of the preparations with and without collagen.

Biocompatibility and Transfection Efficiency of PAMAM-cmRNA (BMP-2) Dendriplexes in BMSC and MC3T3-E1 Cells:

The cells are seeded at 10,000 cells per well density in a 96 well plate, one day prior to treating with formulations. Next day, the media is replaced with serum-free media and the cells treated with complexes containing cmRNA (BMP-2). Untreated cells act as controls, while cells treated with polyethylenimine are used as a positive control to induce cytotoxicity. The complexes are incubated with the cells for 4 hours and 24 hours to mimic in vitro transfection conditions. At the end of treatment period, old media are replaced with fresh media, followed by addition of MTS [3-(4,5-dimethylthiazol-2-yl)-5-(3-carboxymethoxyphenyl)-2-(4-sulfophenyl)-2Htetrazolium] reagent. The amount of soluble formazan produced by reduction of MTS reagent is measured calorimetrically at 490 nm.

The ability of the synthesized PAMAM-cmRNA (BMP-2) dendriplexes to transfect BMSC and MC3T3-E1 cells is assessed qualitatively using reverse transcriptase polymerase chain reaction (RT-PCR). The transfected cells, after different time points of treatment, are lysed and the expression of bone specific genes (collagen type I, osteocalcin), Cbfa-1 and osterix in the total extracted RNA is determined. Transfection is quantified by measuring the amount of BMP-2 that is released into the culture medium by transfected cells using enzyme linked immunosorbent assay (ELISA). For ELISA, the cells are treated with different preparations for 6 hours, following which, the dendriplexes are removed and cells are washed twice with phosphate buffered saline and are cultured in serum free media for different time points (24, 48, 72, and 96 hours) at 37° C. The amount of BMP-2 secreted by transfected cells into the cell culture medium is determined using sandwich ELISA. In the transfection experiments, PAMAM dendrimers complexed with scrambled cmRNA (BMP-2) are used as a negative control.

Once the RNA transfection is confirmed, the functionality of transfection is determined using cell proliferation and biochemical assays after 2, 3 and 4 weeks, post transfection in MCT3T3-E1 cells, which are highly suited to examine the molecular mechanisms of osteoblast maturation and bone formation (Quarles et al., 1992). The proliferation of transfected cells is assessed using a modified MTT [3-(4, 5-Dimethylthiazol-2-yl)-2, 5-diphenyltetrazolium bromide] assay. Alkaline phosphatase (ALP) activity in the transfected cells is determined by lysing the cells and measuring the enzyme activity using the ALP reagent containing p-nitrophenylphosphate at 405 nm. ALP activity for each sample is normalized using the average cell count, which can be obtained from the cell proliferation assay. Utilizing the interaction of calcium with ocresolphthalein complexone, calcium content in the supernatant of the transfected cells is determined and measured calorimetrically at 570 nm. To further evaluate bone matrix production, the transfected cells are fixed with 10% formaldehyde and stained with Alizarin red S stain and imaged for calcific deposits after 2, 3 and 4 weeks, post transfection.

Once the transfection efficiency of PAMAM-cmRNA (BMP-2) dendriplexes is confirmed, biocompatibility and transfection efficiency of PLGA microspheres incorporating the PAMAM-cmRNA (BMP-2) dendriplexes are determined. PLGA microspheres incorporating the PAMAM-cmRNA (BMP-2) are added to the cells, following which cytotoxicity and transfection efficiency of the delivery system is examined using methods described above. Cells grown in the presence of PLGA microspheres and PLGA microspheres containing PAMAM blank particles are used as controls.

Due to the controlled release mechanism of cmRNA (BMP-2) from PLGA microspheres, the transfection is likely to be prolonged and toxicity minimal when delivered from the microspheres, as compared to dendriplexes delivered alone. cmRNA-dendriplexes may also be absorbed onto the surface of the microspheres after they are prepared as described in Zhan et al. (2007). This approach was shown to prevent pDNA damage that could occur during microparticle synthesis.

Determine the In Vivo Efficacy of a Biomaterial-Based cmRNA (BMP-2) Delivery System to Induce Bone Formation.

After in vitro characterization of the cmRNA delivery system in BMSC and MC3T3-E1 cells, the in vivo efficacy of the system is evaluated using calvarial bone defect (CBD) model in Fisher 344 rats. Animal care and use review approval is obtained prior to beginning in vivo studies. A test preparation with increasing concentrations of cmRNA (BMP-2) is injected into the thigh muscle of the rats and after 3-weeks of implantation, bone formation is assessed using radiographic and histologic analysis.

Specifically, to test the hypothesis that implantation of PLGA microspheres containing PAMAM-cmRNA (BMP-2) dendriplexes into rat calvarial bone defects (CBD) significantly induces bone regeneration, an intramuscular ectopic bone induction model in CBD in Fisher 344 rats is used (15 groups; 7 animals in each group). Collagen (a scaffold for bone regeneration) is used to disperse biomaterials prior to implantation. The test group receives PLGA microspheres incorporating PAMAM-cmRNA (BMP-2) dendriplexes dispersed in collagen. Control groups include animals left with empty defects, animals treated with scaffold containing scrambled RNA of BMP-2 and animals that receive single or different possible combinations of the components of the delivery system including collagen, cmRNA (BMP-2), PAMAM dendrimers, and PLGA microspheres (Table 3). Animals (N=7) in each group are sacrificed after 4 weeks. Bone regeneration in each group is assessed using histology, histomorphometry and micro-computed tomography ($\mu$CT) analysis.

TABLE 3

Treatment groups for in vivo regenerative studies

| Groups | Description |
| --- | --- |
| I | Empty defect |
| II | Collagen |
| III | Recombinant human BMP-2 protein (171 ng/gram of animal) |
| IV | cmRNA (BMP-2) |
| V | Scrambled cmRNA (BMP-2) |
| VI | cmRNA (BMP-2) in collagen |
| VII | Blank PAMAM |
| VIII | Blank PAMAM in collagen |
| IX | PAMAM-cmRNA (BMP-2) dendriplexes in collagen |
| X | PLGA microspheres alone |
| XI | PLGA microspheres in collagen |
| XII | PLGA microspheres containing blank PAMAM |
| XIII | PLGA microspheres containing PAMAM-cmRNA (BMP-2) dendriplexes |
| XIV | PLGA microspheres containing blank PAMAM in collagen |
| XV | PLGA microspheres containing PAMAM-cmRNA (BMP-2) dendriplexes in collagen |

Calvarial Bone Defect Model to Test the In Vivo Efficacy of the Preparations:

CBD model, a well-established orthotopic model with highly suitable anatomy for creating bone defects and to evaluate biomaterials is utilized (Gosain et al., 2000). CBD was shown to be more physiologically relevant than other ectopic bone formation models such as muscle pouch and allows easy comparison with numerous previous studies that utilized this model (Cooper et al., 2010). As mentioned before, PLGA microspheres with or without PAMAM-cmRNA (BMP-2) dendriplexes are dispersed in collagen prior to implantation into the defects. A total of 105 twelve-week old male Fisher 344 rats (about 200 to 250 grams) with 7 rats per group are utilized.

The surgery to create calvarial defects is performed under general anesthesia [(xylazine (5 mg/kg and ketamine (40 mg/kg) or isoflurane (1 to 2.5%)]. The incision area is prepared aseptically and an incision made along the sagittal plane of the cranium with a full thickness flap reflected to expose the calvarial bone. Using trephine bur, a circular defect of 8 mm diameter is created in each rat, under saline irrigation without damaging the dura mater. The disc of calvarial bone is removed. The animals are randomly assigned to one of the 15 groups (see Table 3). After implantation, the periostium and the skin are secured with wound clips or sutures (vicryl), which is removed in 1 to 2 weeks after surgery. Appropriate analgesics (buprenorphine, subcutaneous delivery of 0.01-0.05 mg/kg) and non-steroidal anti-inflammatory drug (meloxicam, 2 mg/kg PO) are utilized to reduce the post-operative discomfort. Topical analgesics (0.5% Bupivacaine) are administered to relieve pain on surgical incisions. All animals (7 per treatment group) are sacrificed after 4 weeks and samples are harvested for image and histological analysis. The timing of sacrifice is chosen based on published studies that showed 3 to 15 weeks to be the critical time to study bone healing in rats (Gosan et al., 2000; Cooper et al., 2010; Huang et al, 2005). The data with nonviral gene delivery systems further confirmed that a 4 week time point captures the early healing events very well. Euthanasia is performed by continuously administering $CO_2$ for at least 15 minutes after respiratory arrest. The method of euthanasia that is proposed is consistent with the recommendations of the American Veterinary Medical Association Guidelines.

Assessment of Bone Regeneration:

Evaluation of bone regeneration is performed using histology, histomorphometry and micro-computed tomography (μCT). After euthanasia, calvarial tissue is harvested, fixed in buffered formalin and subjected to μCT analysis for bone volume measurements. The specimens are then decalcified and subjected to histological and histomorphometric analysis for determination of new bone area percentage.

There will likely be significantly higher bone formation in the calvarial defects treated with PLGA microspheres containing the PAMAM-cmRNA (BMP-2), compared to all the other groups tested.

One-way analysis of variance (ANOVA) is used to assess effects of treatment new bone volume derived from XT analysis and new bone area derived from histomorphometric analysis using a Type I error level of 0.05. Planned pairwise comparisons among treatments is assessed using the Holm modification of the Bonferroni adjustment for multiple comparisons in conjunction with an overall Type I error level of 0.05 (Holm, 1977).

The sample size of 7 animals per treatment was selected based on 14 planned multiple comparisons (Huang et al., 2005) of novel treatment with each of the other treatments, assuming conventional Bonferroni adjustment in conjunction with an overall Type I error level of 0.05, i.e., $\alpha=0.5/14$.

Based on a previous study (Huang et al., 2005), power calculations for pairwise treatment comparisons within a given time are based upon a common standard deviation (SD) of either 2% or 3% bone area regeneration, and indicate good power to detect reasonable effect sizes among treatments.

References

An et al., *Biomaterials*, 21:2635 (2000).
Atluri et al., *Mol. Pharm.*, 12:3032 (2015).
Boyce et al., *Orthop. Clin. No. America*, 30: 571 (1999).
Boyne et al., *J. Oral Maxillo. Surg.*, 63:1693 (2005).
Boyne et al., *J. Oral Maxillofac. Surg.*, 63:1693 (2005).
Boyne, *J. Bone and Joint Surg.*, 83:S146 (2001).
Canalis et al., *J. Clin. Invest.*, 81:277 (1988).
Cancedda et al., *Biomaterials*, 28:4240 (2007).
Cooper et al., *Plastic Reconst. Surg.*, 125:1685 (2010).
Deschaseaux et al., *J. Cell. Mol. Med.*, 14:103 (2010).
Do et al., *Adv. Healthc Mater.*, 4:1742(2015).
Elangovan et al., *Biomaterials*, 35:737 (2014).
Elangovan et al., *J. Biomater. Appl.*, 25:3 (2010).
Esfand & Tomalia, *Drug Discov. Today*, 6:427 (2001).
Evans et al., *J. Cell. Physiol.*, 227:416 (2012).
Evans, *Adv. Drug Deliv. Rev.*, 64:1331 (2012).
Evans, *Exp. Rev. Mol. Med.*, 12:e18 (2010).
Ferkol et al., *J. Clin. Invest.*, 95:493 (1995).
Giannoudis et al., *Injury*, 36:S20 (2005).
Gosain et al., *Plastic Reconst. Surg.*, 106:360 (2000).
Greenwald et al., American Association of Tissue Banks, 2010./BoneGraftSubstitutes.
Haensler & Szoka, *Biocon. Chem.*, 4:372 (1993).
Heller et al., *Adv. Drug Delivery Rev.*, 54:1015 (2002).
Holm, *Scand. J. Statis.*, 6:65 (1979).
Holtkamp et al., *Blood*, 108:4009 (2006).
Hong et al., *Tissue Eng. Meth.*, 17:319 (2011).
Huang et al., *Gene Ther.*, 12:418 (2005).
Ilies et al., *J. Med. Chem.*, 45:99 (2004).
Intra & Salem, *J. Pharm. Sci.*, 99:368 (2010).
Ishii and Akira, *Immunity*, 23:111 (2005).
Jha et al., *J. Control Release*, 209:308 (2015).
Karfeld-Sulzer et al., *J. Control Release*, 203:181 (2015).
Kariko et al., *Immunity*, 23:165 (2005).
Kariko et al., *J. Biol. Chem.*, 279:12542 (2004).
Khan & Lane, *Exp. Opin. Biol. Ther.*, 4:741 (2004).
Kim et al., *J. Control Release*, 206:101 (2015).
Kormann et al., *Nature Biotech.*, 29:154 (2011).
Liu and Reineke, *Bioconj. Chem.*, 17:101 (2006).
Mandal and Rossi, *Nat. Protocols*, 8:568 (2013).
Mauney et al., *Biomaterials*, 26:3173 (2005).
Mays et al., *J. Clin. Invest.*, 123:1216 (2013).
Megeld et al., *Pharma. Res.*, 19:954 (2002).
Mockey et al., *Biochem. Biophys. Res. Commun.*, 340:1062 (2006).
Ponsaerts et al., *Clin. Exp. Immunol.*, 134:378 (2003).
Quarles et al., *J. Bone Miner. Res.*, 7:683 (1992).
Quinlan et al., *J. Control Release*, 198:71 (2015).
Quinlan et al., *J. Control Release*, 207:112 (2015).
Rosen, *Cytokine Growth Factor Rev.*, 20:475 (2009).
Roy et al., *Mol. Ther.*, 7:401 (2003).
Sakou, *Bone*, 22:591 (1998).
Sandberg et al., *Clin. Orthop. Relat. Res.*, 289:292 (1993).
Santos et al., *J. Contr. Rel.*, 134:141 (2009).
Seo et al., *J. Control Release*, 209:67 (2015).
Suliman et al., *J. Control Release*, 197:148 (2015).
Tannoury and An, *Spine J.*, 14:552 (2014).
van der Woude et al., *PNAS*, 94:1160 (1997).
Vo et al., *J. Control Release*, 205:25 (2015).
Wagner et al., *Proc. Nat. Acad. Sci.*, 88:4255 (1991).

TABLE 4

POWER FOR THE OVERALL TEST TO DETECT A
DIFFERENCE AMONG TREATMENT MEANS ASSUMING
Δp = Difference in % bone area regenerated between two means

| SD | 4 | 5 | 6 | 7 | 8 | 9 | 10 |
|---|---|---|---|---|---|---|---|
| 2% | 0.770 | 0.951 | 0.995 | 0.999 | 0.999 | 0.999 | 0.999 |
| 3% | 0.316 | 0.552 | 0.770 | 0.911 | 0.975 | 0.995 | 0.999 |

Wang et al., *J. Control Release*, 206: 232 (2015).
Wang et al., *Mol. Ther.*, 21:358 (2013).
Warren et al., *Cell Stem Cell*, 7:618 (2010).
Wee et al., *Adv. Drug Deliv. Rev.*, 31:267 (1998).
Woo, *J. Oral Maxillo. Surg.*, 70:765 (2012).
Yamamoto et al., *Eur. J. Pharm. Biopharm.*, 71:484 (2009).
Zhang et al., *Biocon. Chem.*, 18:2068 (2007).
Zhou et al., *Chem. Commun.*, 14:2362 (2006).
Zhu et al., *Bioconj. Chem.*, 19:3499 (2008).

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed:

1. A composition comprising chemically modified RNA (cmRNA) encapsulated in or complexed with a non-viral delivery vehicle comprising polyamidoamine (PAMAM) dendrimers or polyethylenimine (PEI) and a biocompatible, bioresorbable scaffold comprising collagen, wherein at least 90% of the cytosine (C) and uridine (U) in the cmRNA are substituted with 5-methylcytidine-5 triphosphate, pseudouridine-5-triphosfate, or a combination thereof, and wherein the composition comprises sequences that encode at least two proteins selected from the group consisting of a BMP, osteocalcin, type I collagen, core binding factor, PDGF, TGF-beta, antibody to sclerostin or the antigen binding fragment thereof, antibody to receptor activator of nuclear factor kappa-B ligand (RANKL) or the antigen binding fragment thereof, osterix, HGF, bFGF, NGF, neuregulin, or activin.

2. The composition of claim 1 wherein the delivery vehicle comprises microparticles or nanoparticles.

3. The composition of claim 1 wherein the delivery vehicle further comprises cationic or non-cationic polymers.

4. The composition of claim 1 wherein the delivery vehicle further comprises PEI, chitosan, cyclodextrin or dendrimers.

5. The composition of claim 1 wherein the delivery vehicle further comprises PLGA, PEI, PLA, or PAMAM.

6. The composition of claim 1 wherein the PEI comprises branched PEI.

7. The composition of claim 1 wherein the delivery vehicle comprises complexes of cmRNA and the PEI.

8. The composition of claim 1 wherein the cmRNA encodes at least one of a BMP or PDGF.

9. The composition of claim 1 wherein the scaffold further comprises proteoglycan, alginate, chitosan or extracellular matrix.

10. The composition of claim 1 wherein the scaffold further comprises a synthetic polymer.

11. The composition of claim 10 wherein the synthetic polymer comprises PLA, PGLA, PLLA or polystyrene.

12. The method of claim 2 wherein the microparticles or nanoparticles comprise PLGA.

13. The method of claim 12 wherein the collagen scaffold comprises the microparticles or nanoparticles which comprise the cmRNA encapsulated in or complexed with PAMAM dendrimers or PEI.

14. A method to enhance tissue regeneration in vivo comprising administering an effective amount of the composition of claim 1 to a tissue of a mammal in need thereof.

15. The method of claim 14 wherein the tissue is bone.

16. The method of claim 14 wherein the composition is administered to a bone defect in the mammal or introduced to the jaw of the mammal.

17. A method to enhance tissue regeneration ex vivo comprising introducing an effective amount of the composition of claim 1 to cells of a mammal.

18. A device coated with the composition of claim 1.

* * * * *